US012573063B2

(12) United States Patent
Gordon et al.

(10) Patent No.: US 12,573,063 B2
(45) Date of Patent: Mar. 10, 2026

(54) SYSTEMS AND METHODS FOR REGISTERING INTRAOPERATIVE IMAGE DATA

(71) Applicant: Intuitive Surgical Operations, Inc., Sunnyvale, CA (US)

(72) Inventors: Lucas S. Gordon, Sunnyvale, CA (US); Julie Walker, San Francisco, CA (US); Troy K. Adebar, San Jose, CA (US); Benjamin G. Cohn, Oakhurst, CA (US); Randall L. Schlesinger, San Mateo, CA (US); Worth B. Walters, Campbell, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 86 days.

(21) Appl. No.: 18/549,819

(22) PCT Filed: Mar. 9, 2022

(86) PCT No.: PCT/US2022/019537
§ 371 (c)(1),
(2) Date: Sep. 8, 2023

(87) PCT Pub. No.: WO2022/192392
PCT Pub. Date: Sep. 15, 2022

(65) Prior Publication Data
US 2024/0153113 A1     May 9, 2024

Related U.S. Application Data

(60) Provisional application No. 63/159,188, filed on Mar. 10, 2021.

(51) Int. Cl.
*A61B 8/00*     (2006.01)
*A61B 8/12*     (2006.01)
(Continued)

(52) U.S. Cl.
CPC ................ *G06T 7/337* (2017.01); *A61B 8/12* (2013.01); *A61B 8/4254* (2013.01); *A61B 8/54* (2013.01);
(Continued)

(58) Field of Classification Search
CPC . G06T 7/337; G06T 7/74; G06T 2207/10132; A61B 8/12; A61B 8/4254;
(Continued)

(56) References Cited

U.S. PATENT DOCUMENTS

| | | | | | |
|---|---|---|---|---|---|
| 5,243,988 | A | * | 9/1993 | Sieben | ................... A61B 8/445 600/463 |
| 6,380,732 | B1 | | 4/2002 | Gilboa | |

(Continued)

FOREIGN PATENT DOCUMENTS

| | | |
|---|---|---|
| CN | 101375805 A | 3/2009 |
| CN | 100515332 C | 7/2009 |

(Continued)

OTHER PUBLICATIONS

International Search Report and Written Opinion for Application No. PCT/US2022/019537, mailed Jun. 9, 2022, 14 pages.
(Continued)

*Primary Examiner* — Michael J Carey
*Assistant Examiner* — Zainab Mohammed Aldarraji
(74) *Attorney, Agent, or Firm* — Haynes & Boone, LLP.

(57) ABSTRACT

A medical system comprises an elongate device, an elongate sheath configured to extend within the elongate device, and an imaging probe configured to extend within the elongate sheath. The elongate sheath includes an identification feature. The medical system further comprises a control system configured to receive imaging data from the imaging probe. The imaging data is captured by the imaging probe. The control system is further configured to analyze the imaging
(Continued)

data to identify an appearance of the identification feature within the imaging data. The control system is further configured to, based on the appearance of the identification feature, register the imaging data to a reference frame of the elongate device.

24 Claims, 17 Drawing Sheets

(51) Int. Cl.
    *G06T 7/33*        (2017.01)
    *G06T 7/73*        (2017.01)
(52) U.S. Cl.
    CPC ...... *G06T 7/74* (2017.01); *G06T 2207/10132* (2013.01)
(58) Field of Classification Search
    CPC ......... A61B 8/54; A61B 8/445; A61B 8/0841; A61B 8/4494; A61B 8/5207
    See application file for complete search history.

(56)                    References Cited

U.S. PATENT DOCUMENTS

| | | | |
|---|---|---|---|
| 6,389,187 B1 | 5/2002 | Greenaway et al. | |
| 6,468,265 B1 | 10/2002 | Evans et al. | |
| 7,206,462 B1 | 4/2007 | Betke et al. | |
| 7,506,650 B2 | 3/2009 | Lowe et al. | |
| 7,725,214 B2 | 5/2010 | Diolaiti | |
| 7,772,541 B2 | 8/2010 | Froggatt et al. | |
| 7,781,724 B2 | 8/2010 | Childers et al. | |
| 7,930,065 B2 | 4/2011 | Larkin et al. | |
| 8,062,212 B2 | 11/2011 | Belson | |
| 8,226,546 B2 | 7/2012 | Belson | |
| 8,248,414 B2 | 8/2012 | Gattani et al. | |
| 8,303,505 B2 | 11/2012 | Webler et al. | |
| 8,317,746 B2 | 11/2012 | Sewell et al. | |
| 8,361,090 B2 | 1/2013 | Belson | |
| 8,398,541 B2 | 3/2013 | Dimaio et al. | |
| 8,517,923 B2 | 8/2013 | Belson et al. | |
| 8,611,983 B2 | 12/2013 | Glossop et al. | |
| 8,900,131 B2 | 12/2014 | Chopra et al. | |
| 9,452,276 B2 | 9/2016 | Duindam et al. | |
| 10,542,868 B2 | 1/2020 | Gordon et al. | |
| 11,266,387 B2 | 3/2022 | Walters et al. | |
| 2002/0115941 A1 | 8/2002 | Whayne et al. | |
| 2002/0133057 A1 | 9/2002 | Kukuk | |
| 2003/0085890 A1 | 5/2003 | Baumberg et al. | |
| 2003/0093067 A1 | 5/2003 | Panescu | |
| 2004/0254458 A1 | 12/2004 | Govari | |
| 2005/0182295 A1 | 8/2005 | Soper et al. | |
| 2006/0013523 A1 | 1/2006 | Childers et al. | |
| 2006/0025677 A1 | 2/2006 | Verard et al. | |
| 2006/0239544 A1 | 10/2006 | Yankelevitz et al. | |
| 2007/0038062 A1 | 2/2007 | Redel | |
| 2007/0167801 A1 | 7/2007 | Webler et al. | |
| 2007/0237373 A1 | 10/2007 | Kiraly et al. | |
| 2007/0249911 A1 | 10/2007 | Simon | |
| 2007/0293734 A1 | 12/2007 | Coste-Maniere et al. | |
| 2008/0082109 A1 | 4/2008 | Moll et al. | |
| 2008/0123922 A1 | 5/2008 | Gielen et al. | |
| 2008/0178654 A1 | 7/2008 | Hochmitz | |
| 2008/0255505 A1 | 10/2008 | Carlson et al. | |
| 2008/0287803 A1 | 11/2008 | Li et al. | |
| 2008/0294034 A1 | 11/2008 | Krueger et al. | |
| 2009/0062813 A1 | 3/2009 | Prisco et al. | |
| 2009/0156895 A1 | 6/2009 | Higgins et al. | |
| 2009/0163810 A1 | 6/2009 | Kanade et al. | |
| 2009/0171184 A1 | 7/2009 | Jenkins et al. | |
| 2009/0227861 A1 | 9/2009 | Ganatra et al. | |
| 2009/0262980 A1 | 10/2009 | Markowitz et al. | |
| 2009/0268010 A1 | 10/2009 | Zhao et al. | |
| 2010/0249506 A1 | 9/2010 | Prisco | |

| | | | |
|---|---|---|---|
| 2011/0112569 A1 | 5/2011 | Friedman et al. | |
| 2011/0207997 A1 | 8/2011 | Greenburg et al. | |
| 2011/0237940 A1 | 9/2011 | Raleigh | |
| 2011/0282140 A1 | 11/2011 | Itkowitz et al. | |
| 2012/0004533 A1 | 1/2012 | Peng et al. | |
| 2012/0035438 A1 | 2/2012 | Ferren et al. | |
| 2012/0059378 A1 | 3/2012 | Farrell | |
| 2012/0065481 A1 | 3/2012 | Hunter et al. | |
| 2012/0203067 A1 | 8/2012 | Higgins et al. | |
| 2012/0289843 A1 | 11/2012 | Chopra et al. | |
| 2012/0296620 A1 | 11/2012 | Aulbach | |
| 2012/0327204 A1 | 12/2012 | Friedman et al. | |
| 2012/0330622 A1 | 12/2012 | Butson et al. | |
| 2013/0085774 A1 | 4/2013 | Chen et al. | |
| 2013/0267848 A1* | 10/2013 | Fearnot ................... A61B 8/12 606/200 |
| 2013/0303876 A1 | 11/2013 | Gelfand et al. | |
| 2014/0187949 A1* | 7/2014 | Zhao ..................... A61B 10/04 600/443 |
| 2014/0188440 A1 | 7/2014 | Donhowe et al. | |
| 2014/0276020 A1 | 9/2014 | Hutchins et al. | |
| 2015/0094914 A1 | 4/2015 | Abreu | |
| 2015/0221105 A1 | 8/2015 | Tripathi et al. | |
| 2015/0347682 A1 | 12/2015 | Chen et al. | |
| 2017/0132812 A1 | 5/2017 | Tripathi et al. | |
| 2018/0000314 A1* | 1/2018 | Saadat .............. A61B 1/00085 |
| 2018/0235709 A1 | 8/2018 | Donhowe et al. | |
| 2018/0240237 A1 | 8/2018 | Donhowe et al. | |
| 2019/0142528 A1* | 5/2019 | Vertikov ........... A61B 1/00172 600/424 |

FOREIGN PATENT DOCUMENTS

| | | |
|---|---|---|
| CN | 101862205 A | 10/2010 |
| CN | 102186404 A | 9/2011 |
| CN | 102481115 A | 5/2012 |
| CN | 102740755 A | 10/2012 |
| CN | 102740791 A | 10/2012 |
| EP | 1481637 A1 | 12/2004 |
| EP | 1779802 A2 | 5/2007 |
| EP | 2238901 A2 | 10/2010 |
| EP | 2377457 A1 | 10/2011 |
| JP | 2009542374 A | 12/2009 |
| JP | 2010540021 A | 12/2010 |
| JP | 2011525827 A | 9/2011 |
| WO | WO-2005082246 A1 | 9/2005 |
| WO | WO-2006124388 A1 | 11/2006 |
| WO | WO-2009023801 A1 | 2/2009 |
| WO | WO-2010049834 A1 | 5/2010 |
| WO | WO-2010078009 A1 | 7/2010 |
| WO | WO-2014106253 A1 | 7/2014 |
| WO | WO-2016025465 A1 | 2/2016 |
| WO | WO-2018195216 A1 | 10/2018 |
| WO | WO-2019209767 A1 | 10/2019 |

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

International Preliminary Report on Patentability for Application No. PCT/US2022/019537 mailed Sep. 21, 2023, 08 pages.

Extended European Search Report for Application No. 13867391.8, mailed on Jul. 22, 2016, 7 pages.

Extended European Search Report for Application No. 13868283.6, mailed on Jul. 26, 2016, 7 pages.

Extended European Search Report for Application No. 18188100.4, mailed on Nov. 13, 2018, 8 pages.

International Search Report and Written Opinion for Application No. PCT/US13/78497, mailed on Apr. 28, 2014, 14 pages.

International Search Report and Written Opinion for Application No. PCT/US13/78508, mailed on Apr. 3, 2014, 15 pages.

Office Action mailed Dec. 28, 2016 for Chinese Application No. 201380068398.6 filed Dec. 31, 2013, 18 pages.

Wen R., et al., "Robot-Assisted RF Ablation with Interactive Planning and Mixed Reality Guidance," IEEE/SICE International Symposium on System Integration, 2012, pp. 31-36.

(56)     References Cited

OTHER PUBLICATIONS

Yaniv Z., et al., "Needle-Based Interventions With the Image-Guided Surgery Toolkit (IGSTK): From Phantoms to Clinical Trials," IEEE Transactions on Biomedical Engineering, 2010, vol. 57 (4), pp. 922-933.
Extended European Search Report for Application No. EP25158896. 8, mailed on May 9, 2025, 10 pages.

\* cited by examiner

400

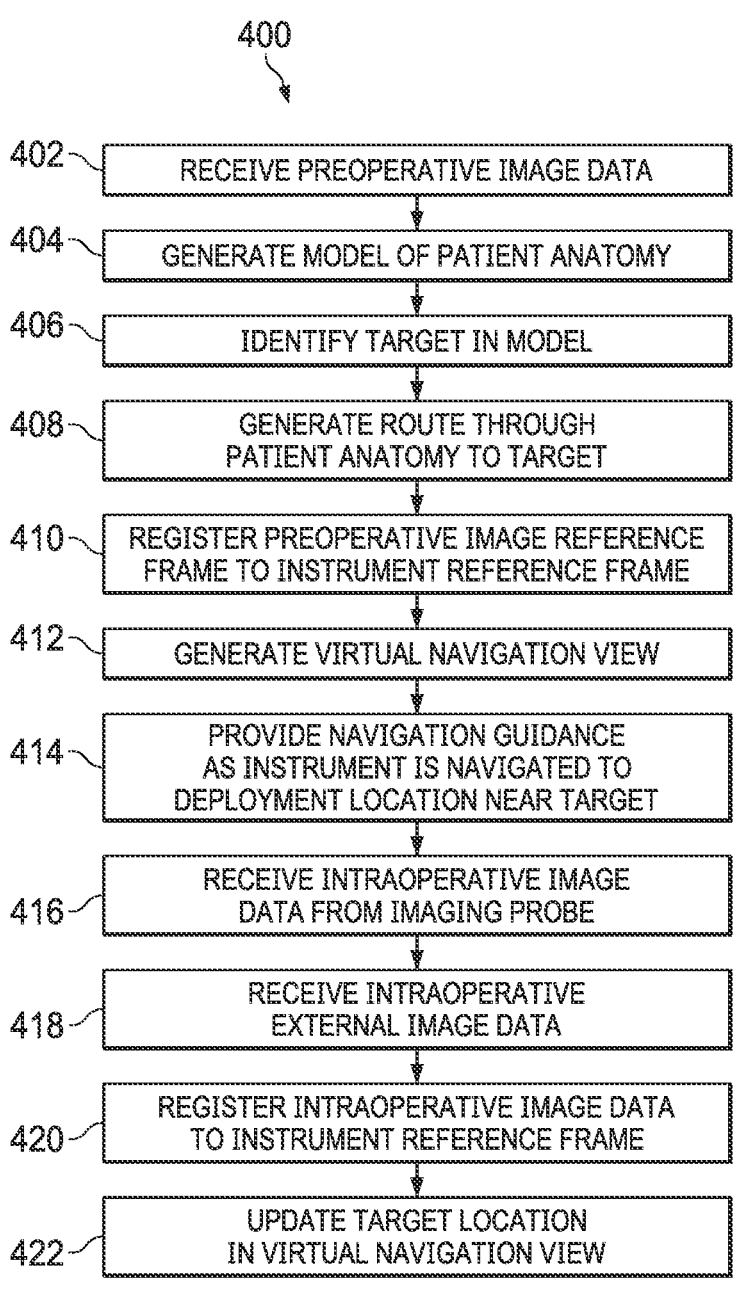

402 — RECEIVE PREOPERATIVE IMAGE DATA

404 — GENERATE MODEL OF PATIENT ANATOMY

406 — IDENTIFY TARGET IN MODEL

408 — GENERATE ROUTE THROUGH PATIENT ANATOMY TO TARGET

410 — REGISTER PREOPERATIVE IMAGE REFERENCE FRAME TO INSTRUMENT REFERENCE FRAME

412 — GENERATE VIRTUAL NAVIGATION VIEW

414 — PROVIDE NAVIGATION GUIDANCE AS INSTRUMENT IS NAVIGATED TO DEPLOYMENT LOCATION NEAR TARGET

416 — RECEIVE INTRAOPERATIVE IMAGE DATA FROM IMAGING PROBE

418 — RECEIVE INTRAOPERATIVE EXTERNAL IMAGE DATA

420 — REGISTER INTRAOPERATIVE IMAGE DATA TO INSTRUMENT REFERENCE FRAME

422 — UPDATE TARGET LOCATION IN VIRTUAL NAVIGATION VIEW

FIG. 4

SYSTEMS AND METHODS FOR REGISTERING INTRAOPERATIVE IMAGE DATA

CROSS-REFERENCED APPLICATIONS

This patent application is the U.S. national phase of International Application No. PCT/US2022/019537, filed Mar. 9, 2022, which designated the U.S. and claims priority to and the benefit of U.S. Provisional Application No. 63/159,188, filed Mar. 10, 2021, and entitled "Systems and Methods for Registering Intraoperative Image Data," each of which is incorporated by reference herein in its entirety.

FIELD

Examples described herein relate to systems for registering intraoperative image data, such as an intraoperative image captured by an imaging probe, to a medical instrument reference frame during a medical procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted.

SUMMARY

Various features may improve the effectiveness of minimally invasive imaging instruments including coupling members that allow controlled movement and temporary storage systems for use during a medical procedure. The following presents a simplified summary of various examples described herein and is not intended to identify key or critical elements or to delineate the scope of the claims.

Consistent with some examples, a medical system is provided. The medical system includes an elongate device, an elongate sheath configured to extend within the elongate device, and an imaging probe configured to extend within the elongate sheath. The elongate sheath includes an identification feature. The medical system further includes a control system configured to receive imaging data from the imaging probe. The imaging data is captured by the imaging probe. The control system is further configured to analyze the imaging data to identify an appearance of the identification feature within the imaging data. The control system is further configured to, based on the appearance of the identification feature, register the imaging data to a reference frame of the elongate device.

Consistent with some examples, a method is provided. The method includes receiving imaging data from an imaging probe. The imaging data is captured by the imaging probe, and the imaging probe is configured to extend within an elongate sheath. The elongate sheath is configured to extend within an elongate device, and the elongate sheath includes an identification feature. The method further includes analyzing the imaging data to identify an appearance of the identification feature within the imaging data. The method further includes, based on the appearance of the identification feature, registering the imaging data to a reference frame of the elongate device.

Other examples include corresponding computer systems, apparatus, and computer programs recorded on one or more computer storage devices, each configured to perform the actions of the methods.

It is to be understood that both the foregoing general description and the following detailed description are illustrative and explanatory in nature and are intended to provide an understanding of the various examples described herein without limiting the scope of the various examples described herein. In that regard, additional aspects, features, and advantages of the various examples described herein will be apparent to one skilled in the art from the following detailed description.

BRIEF DESCRIPTIONS OF THE DRAWINGS

FIG. 4 illustrates a method for updating a location of a target in an anatomic model according to some examples.

Figure 1:
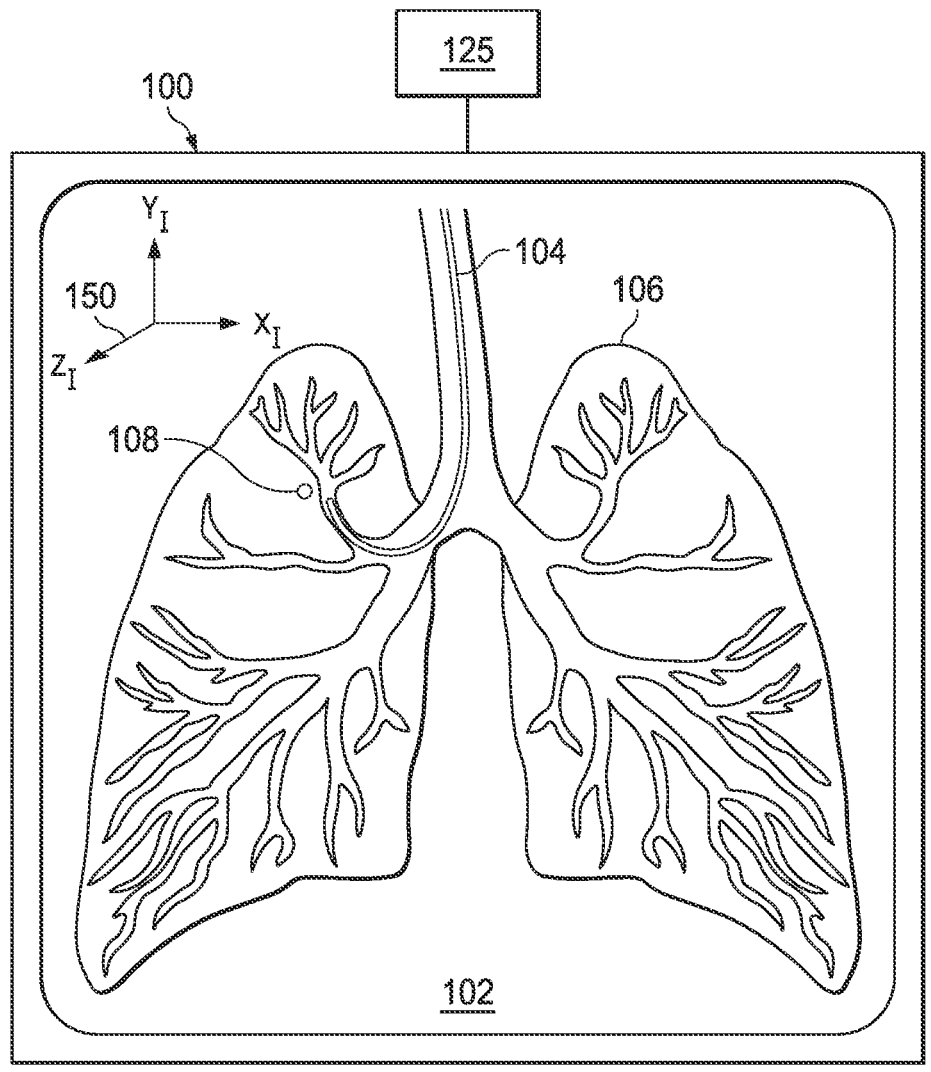
FIG. 1 illustrates an image of a medical instrument registered to an anatomic model according to some examples.

Various examples described herein and their advantages are described in the detailed description that follows. It should be appreciated that like reference numerals are used to identify like elements illustrated in one or more of the FIGURES for purposes of illustrating but not limiting the various examples described herein.

DETAILED DESCRIPTION

The techniques disclosed in this document may be used to register intraoperative image data (which may be referred to as intraoperative imaging data), such as endobronchial ultrasound (EBUS), radial endobronchial ultrasound (REBUS), and/or fluoroscopic imaging data to a medical instrument reference frame during a medical procedure. In some examples, the image data produced by one or more intraoperative imaging devices may be utilized to refine locations of an instrument, an anatomic structure, and/or a target in a model constructed from preoperative imaging. The intraoperative image data may be registered to a reference frame of a medical instrument to assist with determining a rotation, an insertion distance, and/or off-axis bending (e.g., pitch and/or yaw) of the intraoperative imaging device.

With reference to FIG. 1, an image-guided medical procedure, which may be robotic-assisted or otherwise teleoperated, may be conducted in which a display system 100 may display a virtual navigation image 102, which includes an image reference frame $(X_I, Y_I, Z_I)$ 150. An elongate device, such as a medical instrument 104, may be registered (e.g., dynamically referenced) with an anatomic model 106 of a patient derived from preoperative image data obtained, for example, from a computerized tomography (CT) scan. The anatomic model 106 may include a target 108, such as a lesion or nodule of interest, which the procedure is intended to address (e.g., biopsy, treat, view). In some examples, the virtual navigation image 102 may present a physician with a virtual image of the internal surgical site from a viewpoint of the medical instrument 104, such as from a distal tip of the medical instrument 104. In some examples, the display system 100 may present a real-time view from the distal tip of the medical instrument 104, such as when the medical instrument 104 includes an endoscope. In some examples, the medical instrument 104 may be manipulated by a robotic-assisted manipulator controlled by a control system 125, or processing system, which includes one or more processors. An example of a robotic-assisted medical system will be described further at FIG. 11. In some examples, an imaging probe may extend through a lumen of the medical instrument 104.

Generating the virtual navigation image 102 involves the registration of the image reference frame $(X_I, Y_I, Z_I)$ 150 to a surgical reference frame (e.g., frame $X_S, Y_S, Z_S$ of FIG. 11) of the anatomy and/or a medical instrument reference frame (e.g., frame $X_M, Y_M, Z_M$ of FIG. 11) of the medical instrument 104. This registration may rotate, translate, or otherwise manipulate, by rigid or non-rigid transforms, points associated with the segmented instrument shape from the image data and/or points associated with the shape data from a shape sensor disposed along a length of the medical instrument 104. This registration between the image and instrument reference frames may be achieved, for example, by using a point-based iterative closest point (ICP) technique as described in U.S. Pat. App. Pub. No. 2018/0240237, filed on Feb. 12, 2018, entitled "Systems and Methods of Registration for Image-Guided Surgery" and in U.S. Pat. App. Pub. No. 2018/0235709, filed on Feb. 12, 2018, entitled "Systems and Methods of Registration for Image-Guided Surgery," which are incorporated by reference herein in their entireties. The registration may be achieved additionally or alternatively by another point cloud registration technique.

Figure 2:
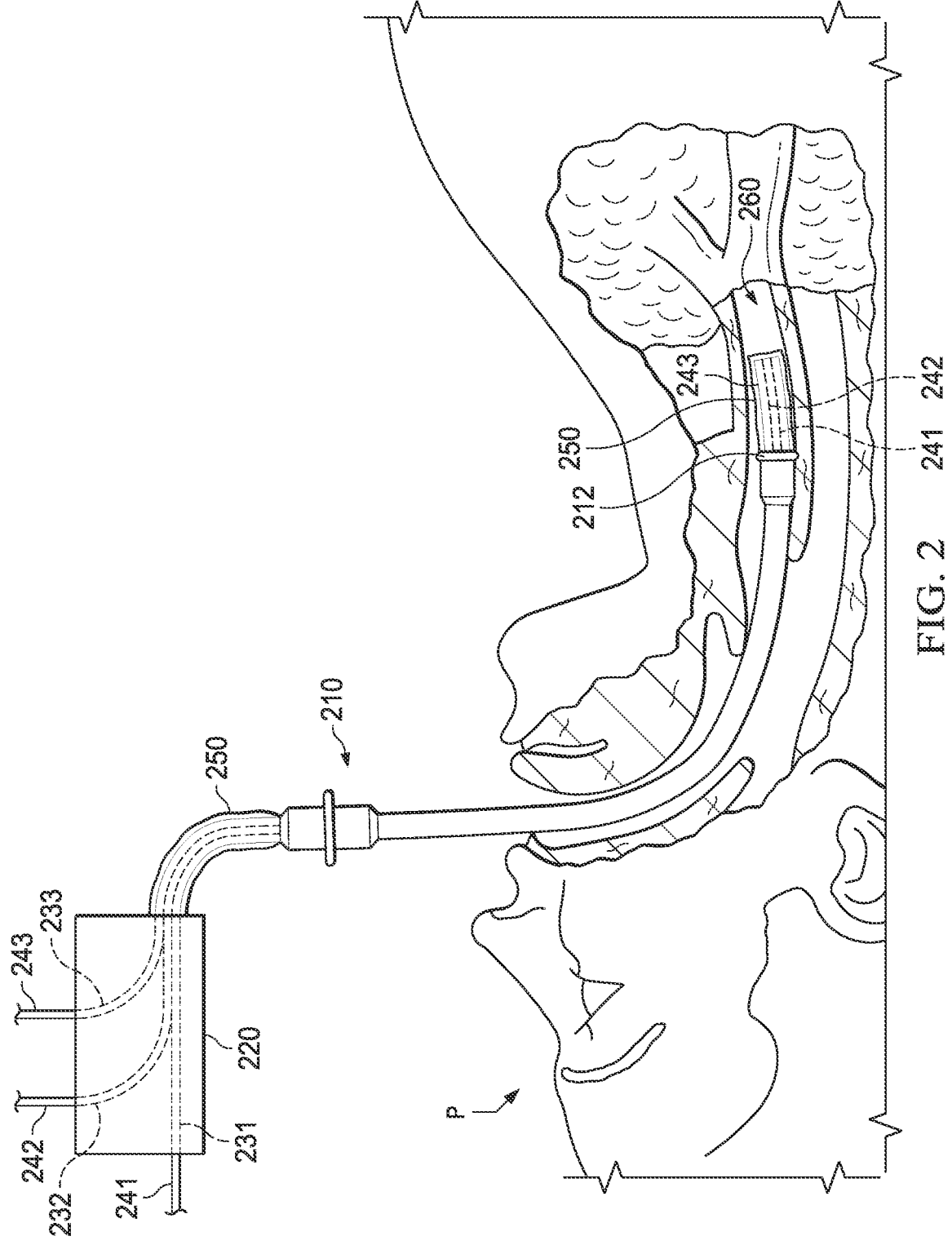
FIG. 2 is a simplified diagram of a medical instrument being introduced into a patient anatomy according to some examples

As shown in FIG. 2, an endotracheal (ET) tube 210 may be used to introduce one or more medical instruments into the airways of a patient P. In order for the ET tube 210 to accommodate more than one medical instrument, a multiport adaptor 220 may be used to align the medical instruments for insertion through the ET tube 210. As shown, the adaptor 220 includes three insertion channels 231, 232, 233 for accepting three medical instruments 241, 242, 243, respectively. Although FIG. 2 shows three insertion channels 231-233 and three medical instruments 241-243, the adaptor 220 may optionally include one channel, two channels, or four or more channels. In some examples, each of the medical instruments 241-243 is an elongate instrument, such as the medical instrument 104 of FIG. 1. In some examples, one or more of the medical instruments 241-243 may be received within a catheter 250. The catheter 250 may be inserted through the ET tube 210 and may extend beyond a distal end 212 of the ET tube 210 into one or more passageways 260 (e.g., airways) of the patient P. Additional details regarding the ET tube 210 may be found in U.S. patent application Ser. No. 16/310,383, filed on Dec. 14, 2018, entitled "Systems and Methods of Integrated Real-Time Visualization," which is incorporated by reference herein in its entirety.

Figure 3:
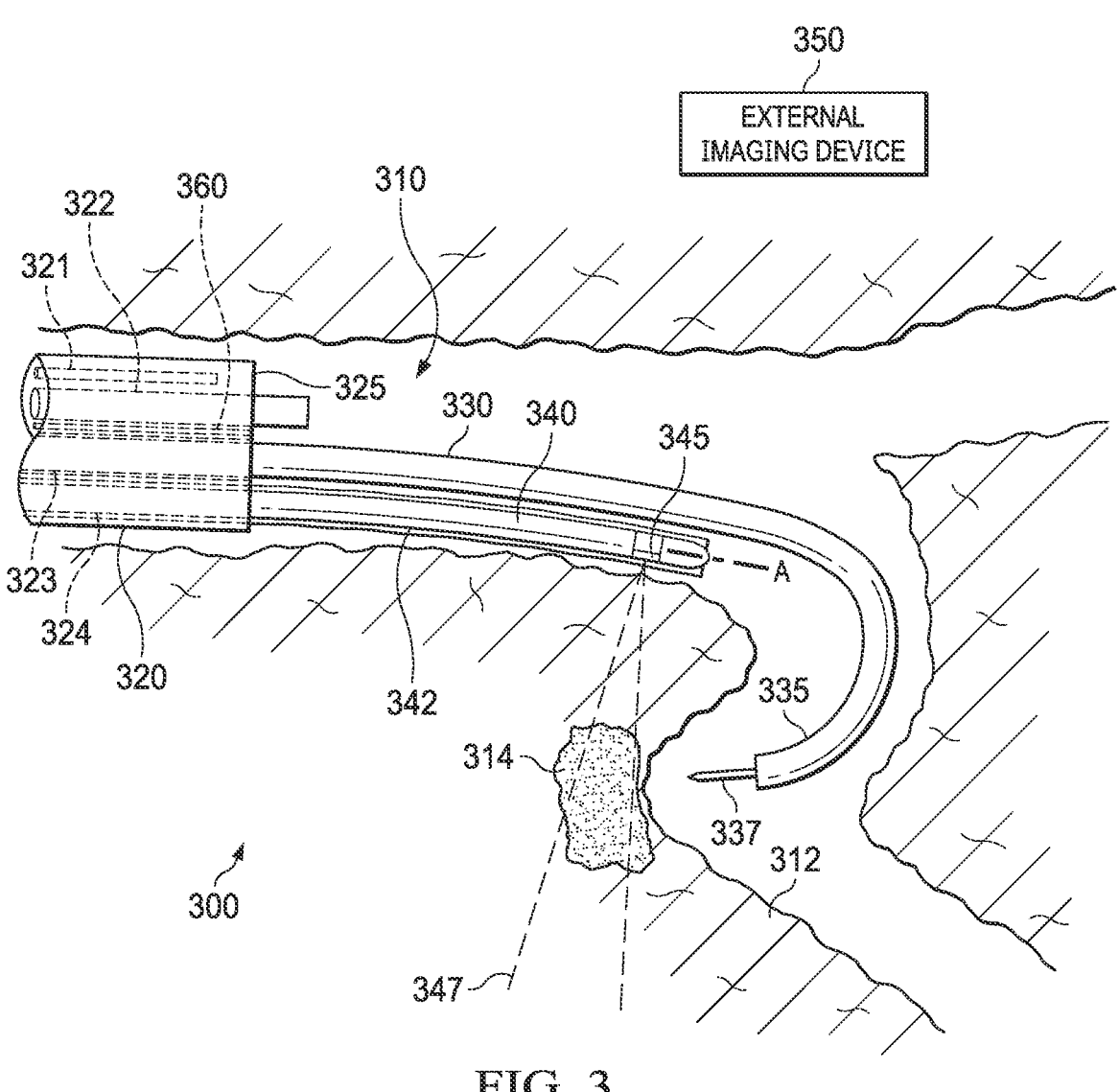
FIG. 3 is a simplified diagram of a side view of a medical instrument within a patient anatomy according to some examples.

FIG. 3 illustrates a medical system 300 that may include an outer catheter 320 through which a working catheter 330, and an imaging probe 340, an inflation lumen 321, and an evacuation lumen 322 may extend. The outer catheter 320 may represent the catheter 250 of FIG. 2. As shown in FIG. 3, a distal end 325 of the outer catheter 320 has been inserted into anatomical passageways 310, which may be the passageways 260, of the patient P. In some examples, the inflation lumen 321 may be used to inflate one or more sealing devices, such as a balloon, to create a seal across one of the passageways 310. The evacuation lumen 322 may be used for removing air from the passageways 310 that are distal to any sealing devices that may be within the passageways 310. The outer catheter 320 may include a working lumen 323 through which the working catheter 330 is inserted. The outer catheter 320 may include an imaging lumen 324 through which the imaging probe 340 may be inserted. Alternatively, the imaging probe 340 may be inserted through the working catheter 330. The working catheter 330 and/or the imaging probe 340 may represent one or more of the medical instruments 241-243 of FIG. 2.

In some examples, the imaging probe 340 may be positioned within an imaging probe sheath 342, which may additionally be inserted into the passageways 310 through the imaging lumen 324. In some examples, the imaging probe 340 may be a radial probe, such as a radial endobronchial ultrasound (radial EBUS or REBUS) probe. The imaging probe 340 may include an imaging device 345 located near its distal end. The imaging device 345 may be a mechanical radial scanning device that is rotated about a longitudinal axis A of the imaging probe 340. The imaging device 345 may obtain images in an imaging field of view 347. In some examples, the field of view 347 represents a scanning direction of the imaging device 345. In some examples, the scanning direction is a 360° circumferential field of view that is perpendicular to the longitudinal axis A of the imaging probe 340. The appearance of one or more objects in the field of view 347 may change as one or more of the position, orientation, and/or insertion distance of the imaging probe 340 changes. In some examples, the images captured by the imaging device 345 in the scanning direction are captured in a scan plane.

In some examples, the imaging device 345 may be an ultrasound transducer. The imaging device 345 may be coupled to one or more electrical wires or optical fibers for activating the ultrasound transducer, modulating its output, capturing return signals, and/or the like. In some examples, the imaging probe 340 may include side-facing transducers, forward-facing transducers, curved transducers, and/or the like. In some examples, the imaging probe 340 may include one or more electronically phased, mechanically scanned, and/or mechanically steerable transducer elements and/or arrays of transducer elements that are capable of capturing 2D, 3D, and/or 4D ultrasound images in proximity to the distal end of the imaging probe 340.

As further shown in FIG. 3, the medical system 300 may include a tool 337, which may be inserted into the passageways 310 through the working catheter 330. The tool 337 may extend beyond a distal end 335 of the working catheter 330. The tool 337 may be a biopsy tool (e.g., a biopsy needle), an endoscopic instrument or other imaging device, an ultrasound probe, or any other medical tool. In some examples, the medical system 300 may include an external imaging device 350, which may be an intraoperative external imaging device. The external imaging device 350 may be a fluoroscopy imaging device than generates intraoperative fluoroscopy image data, although any suitable imaging technique, such as conventional CT or cone beam CT ("CBCT") techniques, may be used without departing from the examples of the present disclosure.

As shown in FIG. 3, the passageways 310 may be surrounded by tissue 312. Located within the tissue 312 is a region of interest 314, which may correspond to a lesion, a tumor, and/or any other anatomical target (e.g., the target 108 of FIG. 1). Thus, the region of interest 314 may also be referred to herein as an anatomical target 314 or a target 314. As shown in FIG. 3, one or both of the working catheter 330 or the imaging probe 340 may be navigated within the passageways 310 to a location near the target 314. For example, the outer catheter 320 may be steered to position the outer catheter 320 where desired within the passageways 310. In some examples, the distal end 325 of the outer catheter 320 may be navigated to a deployment location near the target 314. Navigation may be performed manually by a user with provided navigation guidance, automatically by the control system, or via a combination of both. As shown in FIG. 3, the distal end 325 may be steered to orient the distal end 325 toward the target 314.

In some examples, a position sensor system and/or a shape sensor 360 may extend within the outer catheter 320. The shape sensor 360 may extend through the outer catheter 320 to the distal end 325 of the outer catheter 320. In some examples, the shape sensor 360 may be used to register the outer catheter 320 to one or more preoperative or intraoperative images and/or models of the patient anatomy (e.g., the model 106 of FIG. 1) and to provide real time localization of the outer catheter 320 to help guide the navigation of the outer catheter 320. The shape sensor 360 may be a fiber optic shape sensor or any other position sensor. For example, the shape sensor 360 may be used to provide real-time shape data (e.g., information regarding a shape of the outer catheter 320 and/or a position of one or more points along the length of the outer catheter 320). This shape data may be utilized to register the outer catheter 320 to the reference frame 150 of the preoperative image data (e.g., to the 3D model constructed from the preoperative image data) and to track a location of the outer catheter 320 during use. Additionally or alternatively, the reference frame 150 of the preoperative image data may be registered to a reference frame of the working catheter 330. In some examples, the reference frame of the outer catheter 320 and the reference frame of the working catheter 330 are a common reference frame. The discussion above with respect to the navigation of the outer catheter 320 may also apply to navigation of the working catheter 330.

In some examples, a position sensor system and/or a shape sensor (not shown) may extend within the imaging probe 340. The shape sensor may extend through the imaging probe 340 to a distal end of the imaging probe 340. Similar to the outer catheter 320 and the working catheter 330, the shape sensor of the imaging probe 340 may be used to register the imaging probe 340 to the one or more preoperative or intraoperative images to provide real time localization of the imaging probe 340 to help guide the operator in positioning and/or orienting the imaging device 345 to take images of the target 314. Additionally or alternatively, the imaging device 345 may capture images of the outer catheter 320, the distal end 325, the working catheter 330, the sheath 342, and/or one or more fiducial markers located on the outer catheter 320 and/or the sheath 342 to aid in registering the imaging probe 340 and/or localizing the imaging probe 340 relative to the target 314 and/or to the outer catheter 320. Additional details regarding the outer catheter 320, the working catheter 330, and the imaging probe 340 are discussed in U.S. patent application Ser. No. 16/310,383, filed on Dec. 14, 2018, entitled "Systems and Methods of Integrated Real-Time Visualization," which is incorporated by reference herein in its entirety.

As shown in FIG. 3, the imaging probe 340 is positioned within the passageways 310 where the imaging device 345 may take intraoperative and real-time images of the target 314. For example, with the imaging probe 340 positioned in close proximity to the target 314, an intraoperative external imaging scan may be performed. As discussed above, in some alternative examples, the imaging probe 340 may be extended out from the distal end 335 of the working catheter 330. For example, the imaging probe 340 may replace the tool 337 or may be positioned adjacent the tool 337 within the working catheter 330. In some examples, while the imaging probe 340 is within the sheath 342, the imaging probe 340 may replace the tool 337 or may be positioned adjacent the tool 337 within the working catheter 330.

FIG. 4 illustrates a method 400 for updating a location of a target in an anatomic model according to some examples. For example, updating the location of the target may generally include updating the location based on intraoperative external image data. One or more of the method steps may be performed on the same robotic-assisted medical system used to perform a biopsy or other medical procedure. The method 400 is illustrated as a set of operations or processes 402 through 422 and is described with continuing reference to FIGS. 1-3 and 5A-10C.

At a process 402, preoperative image data is received at a control system (e.g., the control system 125). For example, a CT scan of the patient anatomy may be performed with a CT scanner, and the CT image data may be received by the control system. Alternatively, preoperative image data may be received from other types of imaging systems including magnetic resonance imaging (MRI) systems, fluoroscopy systems, or any other suitable method for obtaining dimensions of anatomic structures. At a process 404, a three-dimensional (3D) model of the anatomic structures (e.g., the anatomic model 106 of FIG. 1) may be constructed from the preoperative image data by the control system. At a process 406, a target may be identified in the 3D model and/or in the preoperative image data from which it was constructed. For example, the target 108 of FIG. 1 may be identified in the anatomic model 106 as a region of interest for investigation and/or treatment. The target may be automatically identified by the control system and confirmed by a user, or the target may be visually identified by the user and manually selected or indicated in the 3D model, for example, via the display system 100. At a process 408, a route through anatomic passageways formed in the anatomic structures is generated. The route may be generated automatically by the control system. Additionally or alternatively, the control system may generate the route based on one or more user inputs. The route may indicate a path along which the medical instrument 104, for example, may be navigated into close proximity with the target. In some examples, the route may be stored in a control system (e.g., in a memory of a control system) and incorporated into the images displayed on the display system 100.

As discussed above, to provide accurate navigation through the anatomic passageways 310, the reference frame 150 of the preoperative image data (and subsequently constructed 3D model) may be registered to the reference frame of the outer catheter 320 at a process 410. Upon successful registration, a process 412 may include generating a virtual navigation view (e.g., the virtual navigation view 810 of FIG. 10A).

At a process 414, navigation guidance is provided as the outer catheter 320 is navigated through the passageways 310 to a predetermined deployment location in proximity to the target 314. At a process 416, the control system may receive intraoperative image data from the imaging probe 340 (e.g., from the imaging device 345). At a process 418, intraoperative external image data may be received at a control system from an intraoperative external imaging system, such as the external imaging device 350. The intraoperative external image data may be displayed (e.g., in a GUI 800 of FIG. 10A) as an intraoperative external image, such as a fluoroscopic image.

The outer catheter 320 and the imaging probe 340 may be identified in the intraoperative external image. The identification may be made by the control system (e.g., using image processing) and/or by an operator. In order to register the intraoperative external image data to the outer catheter 320, while the intraoperative external imaging is performed, shape data from the outer catheter 320 captured during the intraoperative external imaging process 418 may be received. The shape data may be captured for only a brief period of time or may be captured during the whole image capture period of the intraoperative external imaging process.

At a process 420, the intraoperative image data captured by the imaging probe 340 may be registered to the reference frame of the outer catheter 320. The intraoperative image data may include intraoperative images captured by the imaging probe 340. Each intraoperative image may be registered to the reference frame of the outer catheter 320. Further details regarding the registration between the intraoperative image data captured by the imaging probe 340 and the reference frame of the outer catheter 320 will be discussed below with respect to FIGS. 5A-9F. For example, systems and techniques will be described that identify a rotation of the intraoperative images relative to the outer catheter 320. Additionally, systems and techniques will be described that measure the insertion distance of the imaging probe 340 relative to the distal end 325 of the outer catheter

320. In some examples, the control system may determine and/or measure the insertion distance of the imaging probe 340 to assist with registering the imaging data captured by the imaging probe 340 to the reference frame of the outer catheter 320.

As discussed in more detail below, in some examples, an appearance of one or more identification features may be identified in the imaging data captured by the imaging probe 340. For example, a shape of the identification feature(s), a location of the identification feature(s), and/or any other component regarding how the identification feature(s) looks may be identified in the imaging data captured by the imaging probe 340. The intraoperative image data captured by the imaging probe 340 may be registered to the reference frame of the outer catheter 320 based on the appearance of the one or more identification features. In some examples, one or more objects captured in the intraoperative image data, e.g., a location of an anatomical target, may be registered to the reference frame of the outer catheter 320 based on the appearance of the identification feature(s).

Systems and techniques will also be described that identify the bending (e.g., pitch and/or yaw) of the intraoperative images relative to the longitudinal axis of the outer catheter 320. Additional systems and techniques will be described that determine an orientation of the imaging device 345 based on an analysis of the intraoperative external image data captured by the external imaging device 350, for example. In some examples, the control system may determine the orientation of the imaging device 345 (and therefore the orientation of a scan plane of the imaging device 345) to assist with registering the imaging data captured by the imaging probe 340 to the reference frame of the outer catheter 320.

At a process 422, the location of the anatomic target 108 may be adjusted in the virtual navigation image 102. Additional details regarding updating a location of a target in an anatomic model are described in the U.S. Provisional pat. app. No. 63/133,091, filed on Dec. 31, 2020, entitled "Systems and Methods for Updating a Target Location Using Intraoperative Image Data" and the U.S. Provisional pat. app. No. 63/133,112, filed on Dec. 31, 2020, entitled "Systems and Methods for Updating a Target Location Using Intraoperative Image Data," each of which is incorporated by reference herein in its entirety.

The following discussion will be made with reference to illustrative imaging devices. Various examples of imaging devices are provided in FIGS. 5A-9F. Any one or more of the imaging devices discussed below may include a catheter (e.g., the outer catheter 320 and/or the working catheter 330), an imaging probe (e.g., the imaging probe 340), and/or an imaging probe sheath (e.g., the imaging probe sheath 342). As discussed above with respect to the process 420, the intraoperative image data captured by the imaging probe 340 may be registered to the reference frame of the outer catheter 320. In some examples, the image captured by the imaging probe 340 may be registered to the reference frame of the outer catheter 320 based on the registration between the intraoperative image data captured by the imaging probe 340 and the reference frame of the outer catheter 320, as discussed below. In some examples, based on the registration between the intraoperative image data captured by the imaging probe 340 and the reference frame of the outer catheter 320, a location of the imaging probe 340 may be registered to the reference frame of the outer catheter 320. For example, the position and orientation of the intraoperative image data captured by the imaging probe 340 may be known relative to the position and/or orientation of the imaging probe 340 itself. Therefore, because the position and/or orientation of the intraoperative imaging data captured by the imaging probe 340 is registered to the reference frame of the outer catheter 320, the position and/or orientation of the imaging probe 340 may be registered to the reference frame of the outer catheter 320.

In some examples, a location of the imaging probe sheath 342 may be registered to the reference frame of the outer catheter 320. For example, the position and orientation of the imaging probe 340 may be known relative to the position and/or orientation of the imaging probe sheath 342. Therefore, because the position and/or orientation of the imaging probe 340 is registered to the reference frame of the outer catheter 320, the position and/or orientation of the imaging probe sheath 342 may be registered to the reference frame of the outer catheter 320. In some examples, after the location of the imaging probe sheath 342 is registered to the reference frame of the outer catheter 320, the imaging probe 340 may be removed (e.g., retracted) from the imaging probe sheath 342. One or more additional instruments may then be inserted into the imaging probe sheath 342. The location of the additional instrument(s) may be registered to the imaging probe sheath 342 in a similar manner to the registration process between the location of the imaging probe 340 and the imaging probe sheath 342. Based on the registration between the additional instrument(s) and the imaging probe sheath 342 and/or based on the registration between the location of the imaging probe sheath 342 and the reference frame of the outer catheter 320, the location of the additional instrument(s) may be registered to the reference frame of the outer catheter 320.

Figure 5A:
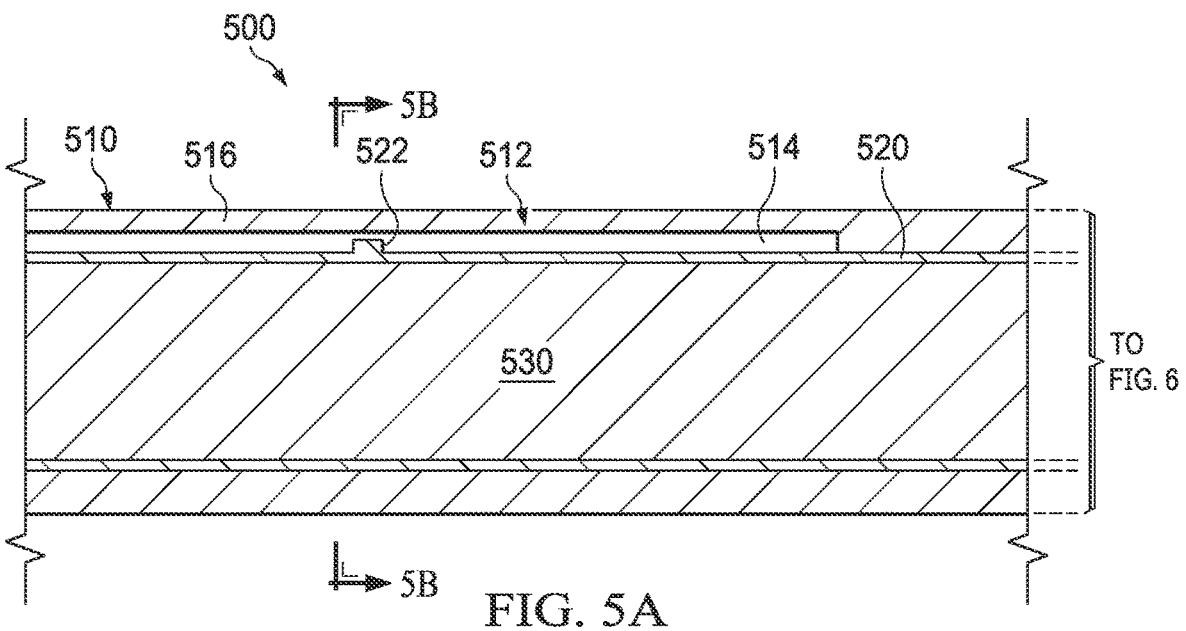
FIGS. 5A and 5B illustrate an imaging device with an imaging probe sheath with a keyed feature according to some examples.
Figure 5B:
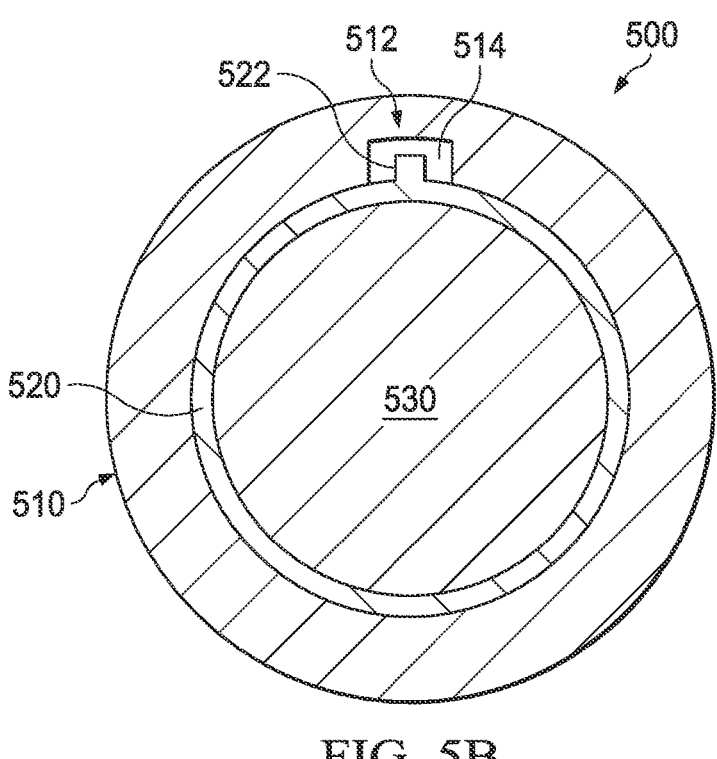

As discussed above, a rotation of the intraoperative images relative to the outer catheter 320 may be identified. FIG. 5A provides a cross-sectional side view of a portion of an imaging device 500, and FIG. 5B provides a cross-sectional view of the imaging device 500 as viewed in a distal direction. The imaging device 500 includes a catheter 510, an imaging probe sheath 520, and an imaging probe 530. In some examples, the catheter 510 may be used as the outer catheter 320, and the imaging probe 530 may be used as the imaging probe 340. The sheath 520 may be movable relative to the catheter 510. In some examples, the imaging probe 530 is movable relative to the sheath 520 and the catheter 510. Alternatively, the imaging probe 530 and the sheath 520 may be axially constrained such that there is no axial movement between the imaging probe 530 and the sheath 520. In such examples, both the imaging probe 530 and the sheath 520 are movable together relative to the catheter 510.

In some examples, the catheter 510 may include a keyed feature 512, which may include a groove 514. The groove 514 may be within a wall 516 of the catheter 510. The groove 514 may be positioned at any location along the length of the catheter 510, such as at a distal portion, a proximal portion, or any portion between the distal portion and the proximal portion. In some examples, the catheter 510 may include more than one keyed feature 512. As shown in FIG. 5A, the sheath 520 may include a corresponding keyed feature 522. In some examples, the keyed feature 522 is a protrusion extending from an outer surface of the sheath 520. The keyed feature 522 of the sheath 520 may be sized to mate with the keyed feature 512 of the catheter 510. For example, the keyed feature 522 may be sized to fit within the groove 514. In alternative examples, the sheath 520 may include one or more grooves, and the catheter 510 may include one or more corresponding protrusions.

In some examples, when the keyed feature 522 is within the groove 514, the sheath 520 may be rotationally constrained relative to the catheter 510. For example, the rotation of the sheath 520 may correspond to the rotation of the catheter 510 when the sheath 520 is positioned within the catheter 510. In such examples, the catheter 510 and the sheath 520 have the same rotational orientation relative to a longitudinal axis of the catheter 510, for example, when the sheath 520 is positioned within the catheter 510. Therefore, the rotational orientation of the sheath 520 is fixed to the rotational orientation of the catheter 510. Thus, the rotational orientation of the sheath 520 may be known in the reference frame of the catheter 510. In some examples, based on this registration, a location of the sheath 520 may be registered to the reference frame of the catheter 510. Therefore, based on the registration between the sheath 520 and the catheter 510, the rotational orientation of the imaging probe 530 may be known in the reference frame of the catheter 510. In some examples, based on this registration, a location of the imaging probe 530 may be registered to the reference frame of the catheter 510. In some examples, the sheath 520 may be rotationally constrained relative to the imaging probe 530. When the sheath 520 is rotationally constrained relative to both the catheter 510 and the imaging probe 530, the catheter 510, the sheath 520, and the imaging probe 530 may all have a common rotational orientation. In such examples, the control system may determine the rotational orientation of the imaging probe 530, for example, based on the rotational orientation of the sheath 520 and/or the catheter 510. Thus, a tracked rotational orientation of the sheath 520 and/or the catheter 510 may provide a known orientation for the imaging probe 530 that is rotationally fixed with respect to the sheath 520 and catheter 510.

Figure 6:
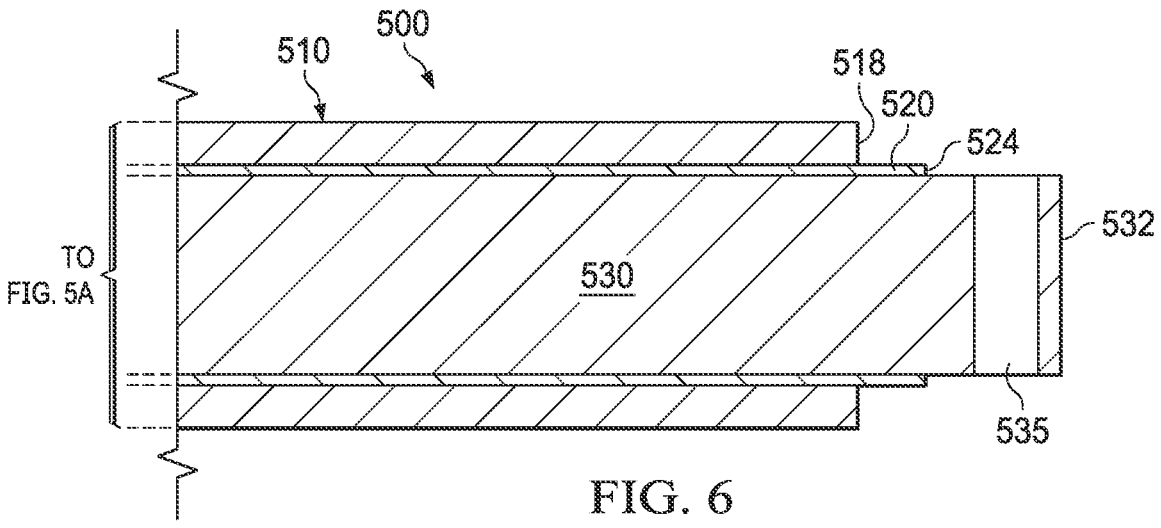
FIG. 6 illustrates an imaging device with an imaging probe extended from an imaging probe sheath, which is extended from a catheter, according to some examples.

In some examples, the catheter 510, the sheath 520, and the imaging probe 530 are independently extendable relative to one another. For example, FIG. 6 illustrates a distal portion (e.g., distal of the portion shown in FIG. 5A) of the imaging device 500 with the sheath 520 extended beyond a distal end 518 of the catheter 510 and illustrates the imaging probe 530 extended beyond a distal end 524 of the sheath 520. The telescoping extension shown in FIG. 6 may increase the available insertion distance of the imaging probe 530. Alternatively, the sheath 520 may be closed at its distal end 524, which prevents the imaging probe 530 from extending beyond the distal end 524. In some examples, such as the example shown in FIG. 6, the catheter 510 and/or the sheath 520 may include the keyed features 512, 522 discussed above with respect to FIGS. 5A and 5B. The catheter 510 and/or the sheath 520 may include any other keyed feature(s). Alternatively, the catheter 510 and/or the sheath 520 might not include keyed features. Any one or more of the catheters and/or sheaths of the imaging devices discussed in the examples below in FIGS. 7A-9F may include keyed features, such as the keyed features 512, 522 and/or any other keyed feature(s) or might not include the keyed features.

In some examples, some or all of the sheath 520 may be rigid. For example, a distal portion of the sheath 520 may be rigid, which may prevent the imaging probe 530 from bending when the imaging probe 530 is positioned within the distal end 524 of the sheath 520. Additionally or alternatively, a rigid distal portion of the sheath 520 may limit the amount of bending of the imaging probe 530 when the imaging probe 530 is extended a small distance beyond the distal end 524 of the sheath 520. In some examples, the bending of the imaging probe 530 may be so limited that it is negligible. In some examples, the rigidity of the sheath

520 may be actively controllable. For example, the control system may send signals to the sheath 520 to control whether the sheath 520 is rigid or flexible. In some examples, the signals from the control system may cause one or more control cables within the sheath 520 to be pulled in a proximal direction, which may cause the sheath 520 to become rigid. Additionally or alternatively, the signals from the control system may cause a rigidizable feature (e.g., a balloon, a rigidizable wire, or any other rigidizable feature) to rigidize, which may cause the sheath 520 to become rigid. The control system may also control which portion(s) of the sheath 520 is rigid and which portion(s) of the sheath 520 is flexible. For example, the control system may cause the distal portion of the sheath 520 to be rigid while maintaining the remainder of the sheath 520 in a flexible state. In some examples, one or more of the rigidizable features discussed above may be positioned at the distal portion of the sheath 520. In such examples, when the rigidizable feature is rigidized, the distal portion of the sheath 520 may become rigid, and the proximal portion of the sheath 520 may remain flexible.

The imaging probe 530 may include an imaging device 535, which may be positioned near a distal end section 532 of the imaging probe 530. The imaging device 535 may be similar to the imaging device 345 discussed above. For example, the imaging device 535 may be an ultrasound transducer. While the imaging device 535 is shown as positioned near the distal end section 532, such as at a distal portion of the imaging probe 530, the imaging device 535 may be positioned at any other position of the imaging probe 530.

Figure 7A:
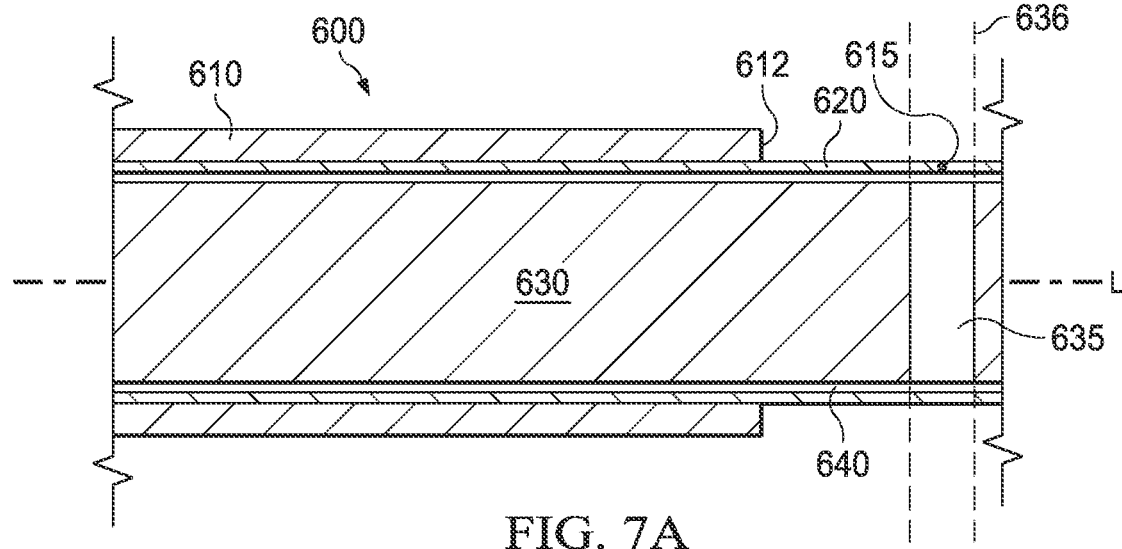
FIGS. 7A-7H illustrate an imaging device with an imaging probe sheath with various identification features according to some examples.

FIG. 7A provides a cross-sectional side view of an imaging device 600. The imaging device 600 includes a catheter 610, an imaging probe sheath 620, and an imaging probe 630. The sheath 620 may be movable in an axial direction relative to the catheter 610, and the imaging probe 630 may be movable in an axial direction relative to the sheath 620. The imaging probe 630 may include an imaging device 635. In some examples, the sheath 620 may include one or more identification features 615. An appearance of the identification feature(s) 615 may be detected by the imaging device 635. For example, a shape of the identification feature(s) 615, a location of the identification feature(s) 615, and/or any other component regarding how the identification feature(s) looks may be identified in the imaging data captured by the imaging device 635. In some examples, the identification feature 615 may be positioned so that at least a portion of the identification feature overlaps a scan plane 636 of the imaging device 635 and thus is visible in the images generated by the imaging device 635. The scan plane (or imaging plane) 636 of the imaging device 635 may extend radially outward from the imaging device 635. In some examples, the scan plane 636 may have a 360° field of view perpendicular to a longitudinal axis L of the imaging probe 630. Further details regarding the identification feature(s) will be discussed below.

The identification feature(s) may be more easily detected by the imaging device 635 when there is good acoustical coupling between the imaging probe 630 and the sheath 620. When the quality of the acoustical coupling increases, the clarity of the image captured by the imaging probe 630 (e.g., captured by the imaging device 635) may increase. In some examples, a cavity 640 may be present between an outer surface of the imaging probe 630 and an inner surface of the sheath 620. The quality of the acoustical coupling between the imaging probe 630 and the sheath 620 may be high when an acoustic impedance of a substance present within the cavity 640 is similar to an acoustic impedance of the patient anatomy within which the imaging probe 630 is located (e.g., the tissue 312). For example, the cavity 640 may be filled with saline. Saline may have an acoustic impedance similar to an acoustic impedance of the patient anatomy within which the imaging probe 630 is located. Therefore, when saline is introduced into the cavity 640, there may be good acoustical coupling between the imaging probe 630 and the sheath 620. While the above discussion is made with respect to saline being introduced into the cavity 640, any other suitable fluid, such as air, may be introduced into the cavity 640. In some examples, air may have an acoustic impedance that is different from the acoustic impedance of the patient anatomy within which the imaging probe 630 is located. In such examples, when air is introduced into the cavity 640, the acoustical coupling between the imaging probe 630 and the sheath 620 may be of a lesser quality than when saline is introduced into the cavity 640.

In some examples, the sheath 620 itself may be made of a material (e.g., one or more PEBA polymers or one or more polyurethane polymers, such as Tecoflex 80A) that has an acoustic impedance that is similar to the acoustic impedance of the patient anatomy within which the imaging probe 630 is located. This may help the identification feature be more visible in the image captured by the imaging probe 630. For example, a greater contrast may be shown between the identification feature and the sheath 620 and/or a difference in color between the identification feature and the sheath 620 may be more defined.

Figure 7B:
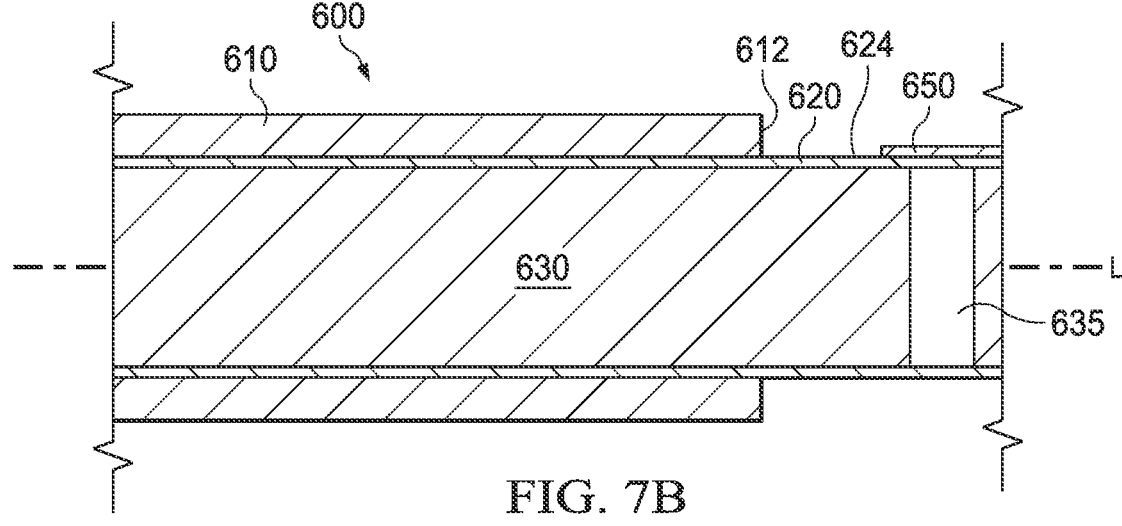
Figure 7C:
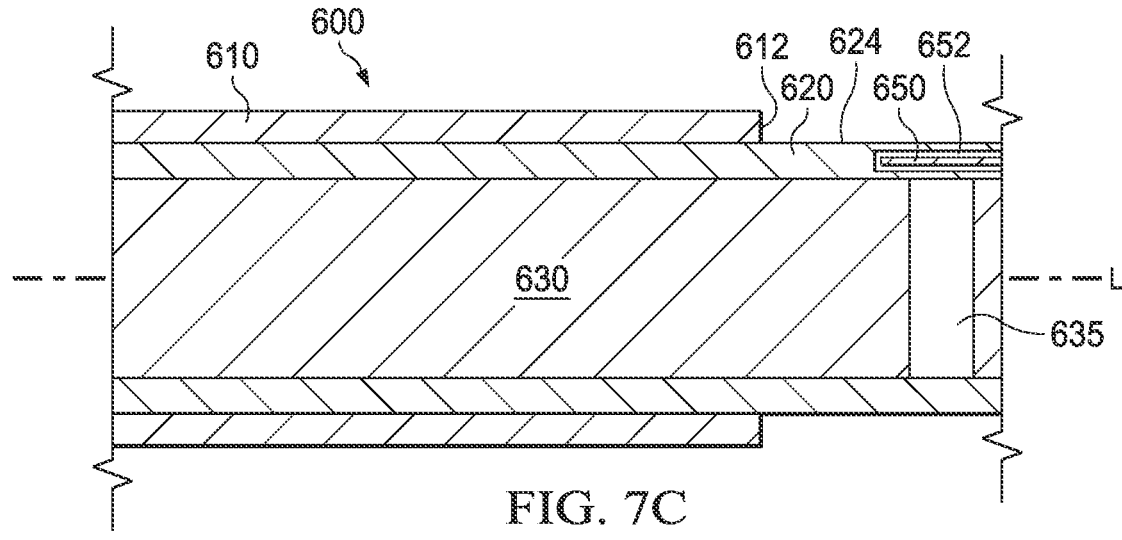

As shown in FIGS. 7B and 7C, the identification feature may be an elongate member 650, which may be an elongate wire. The elongate wire 650 may be positioned outside of the sheath 620 (FIG. 7B) or within a wall 622 of the sheath 620 (FIG. 7C). In some examples, the sheath 620 may include more than one wire 650. The elongate wire 650 may be metal (e.g., tungsten, stainless steel, or any other metallic substance). In some examples, the elongate wire 650 is flat, but may also be cylindrical or any other suitable shape. FIGS. 7B and 7C show the elongate wire 650 extending along a portion of the sheath 620, which may be the distal portion of the sheath 620. Alternatively, the elongate wire 650 may extend along an entire length of the sheath 620. In some examples, the sheath 620 may include multiple elongate wires, and the wires may extend along separate portions of the sheath 620.

In examples when the elongate wire 650 is positioned outside of the sheath 620, as shown in FIG. 7B, the elongate wire 650 may be coupled to an outer surface 624 of the sheath 620. Alternatively, the elongate wire 650 may be coupled to the sheath 620 via one or more connection members (e.g., connection wires, scaffolding, and/or the like) such that the elongate wire 650 is spaced from the outer surface 624 of the sheath 620. In some examples, a portion of the elongate wire 650 may be spaced from the outer surface 624 of the sheath 620, and wherein another portion of the elongate wire 650 may be in contact with the outer surface 624 of the sheath 620. In some examples, the appearance of the elongate wire 650 may be more visible in the image captured by the imaging probe 630 when the elongate wire 650 is positioned outside of the sheath 620 than when the elongate wire 650 is positioned within the wall 622 of the sheath 620. Additionally, a thicker elongate wire 650 may be more visible in the image captured by the imaging probe 630 than a thinner elongate wire 650. In some examples, the elongate wire 650 may have a varying thickness along a length of the elongate wire 650.

As discussed above, the insertion distance of the imaging probe 630 relative to the distal end of the catheter 610 may be measured. For example, the control system may determine the insertion distance of the sheath 620 based on the thickness of the elongate wire 650 that is visible in the image captured by the imaging probe 630. In examples when the sheath 620 and the imaging probe 630 are axially constrained (e.g., the insertion distance of the sheath 620 corresponds to the insertion distance of the imaging probe 630), the control system may determine the insertion distance of the imaging probe 630 based on the insertion distance of the sheath 620.

In some examples, control system may register the imaging data captured by the imaging probe 630 to the reference frame of the catheter 610 based on the insertion distance of the imaging probe 630 relative to the catheter 610. For example, the control system may determine the insertion distance of the imaging probe 630 relative to the sheath 620 based on the appearance of the identification feature (e.g., the elongate wire 650) that is visible in the image captured by the imaging probe 630. The control system may determine the insertion distance of the sheath 620 relative to the catheter 610 as discussed in greater detail below. Based on these relative insertion distance determinations, the control system may determine the insertion distance of the imaging probe 630 relative to the catheter 610. The control system may register the imaging data captured by the imaging probe 630 to the reference frame of the catheter 610 based on the insertion distance of the imaging probe 630 relative to the catheter 610.

In some examples, the appearance of the elongate wire 650 may be identifiable in the intraoperative external image data at different angles around the circumference of the sheath 620. The control system may determine the rotational orientation of the sheath 620 based on the angle at which the appearance of the elongate wire 650 is oriented around the circumference of the sheath 620 in the image captured by the imaging probe 630. In examples when the sheath 620 and the imaging probe 630 are rotationally constrained (e.g., rotationally fixed), the control system may determine the rotational orientation of the imaging probe 630 based on the rotational orientation of the sheath 650. Additionally or alternatively, the control system may determine the rotational orientation of the imaging data captured by the imaging probe 630 relative to the rotational orientation of the sheath 650 based on the appearance of the elongate wire 650 in the imaging data captured by the imaging probe 630.

As discussed above with respect to FIGS. 5A and 5B, in some examples, the rotational orientation of the sheath 650 may be fixed with respect to the rotational orientation of the catheter 610. In such examples, the control system may determine the rotational orientation of the imaging data captured by the imaging probe 630 relative to the rotational orientation of the catheter 610 based on the fixed rotational orientation of the sheath 650 to the rotational orientation of the catheter 610.

In examples when the elongate wire 650 is positioned within the wall 622 of the sheath 620, as shown in FIG. 7C, the elongate wire 650 may be embedded within the wall 622. Alternatively, the elongate wire 650 may be inserted through a lumen 652 in the wall 622. In some examples, the lumen in the wall 622 may be filled with air. Because air has an acoustic impedance that is different from the patient anatomy within which the imaging probe 630 is located, the air-filled lumen (with or without the elongate wire 650 positioned within the lumen) may be identified in the image captured by the imaging device 635 of the imaging probe

630. In some examples, the elongate wire 650 may be inserted into the lumen when the lumen is filled with air. In other examples, the elongate wire 650 may be inserted into the lumen when the lumen is filled with saline or any other fluid.

Figure 7D:
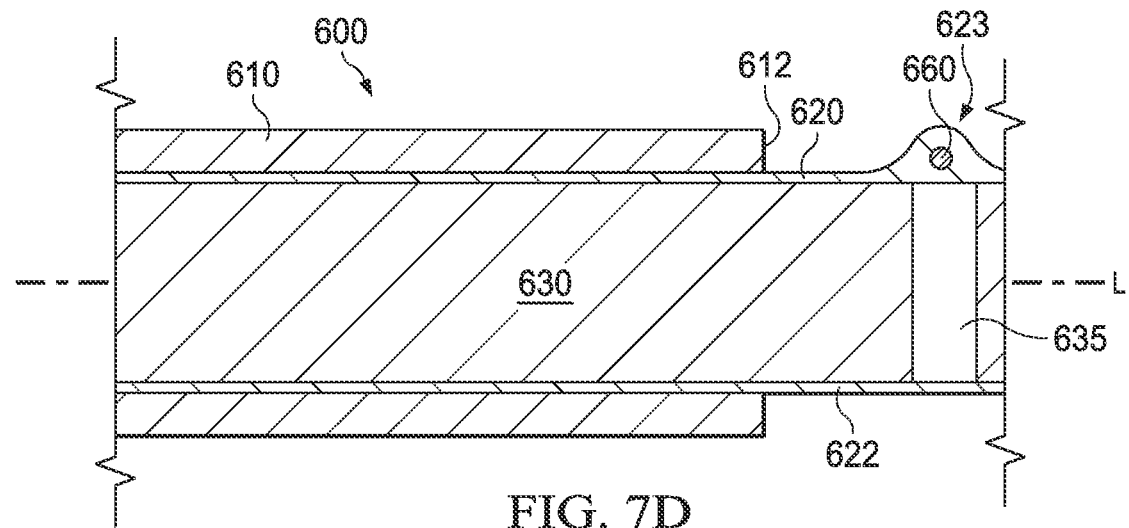

With reference now to FIG. 7D, in some examples, the wall 622 of the sheath 620 may be non-concentric along at least a portion of a length of the sheath 620. For example, a portion 623 of the wall 622 may protrude out from the sheath 620 in a radial direction. As shown in FIG. 7D, the portion 623 may be a non-concentric portion of the wall 622. The identification feature may be positioned within the non-concentric portion 623. In some examples, the identification feature may be a marker 660 positioned within the non-concentric portion 623. In some examples, the marker 660 may be a sphere or other toroidal object. Having a non-concentric portion in the sheath wall may allow for larger identification features to be placed in/on the sheath 620. For example, the marker 660 may be larger (e.g., thicker) than the elongate wire 650 discussed above. Larger identification features may be more visible in the image captured by the imaging probe 630 than smaller identification features.

In some examples, the elongate wire 650 may extend through the non-concentric portion 623. As discussed above, the elongate wire 650 may have a varying thickness along a length of the elongate wire 650. In some examples, a first portion of the elongate wire 650 extends through a concentric portion of the wall 622, and a second portion of the elongate wire 650 extends through the non-concentric portion 623 of the wall 622. The second portion of the elongate wire 650 within the non-concentric portion 623 of the wall 622 may be thicker than the first portion of the elongate wire 650 within the concentric portion of the wall 622. The thicker portion of the elongate wire 650 may be more visible in the image captured by the imaging probe 630 than the thinner portion of the elongate wire 650. In some examples, the second portion of the elongate wire 650 is thinner than the first portion of the elongate wire 650.

Figure 7E:
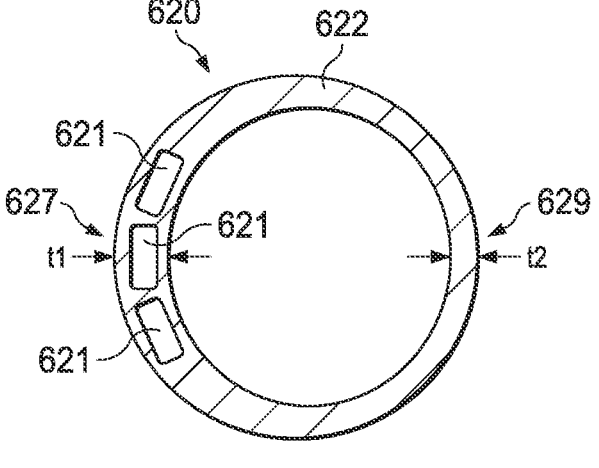

FIG. 7E illustrates a cross-section view of an alternative example of the sheath 620 when viewing the sheath 620 from a distal-looking perspective. As discussed above, the wall 622 of the sheath 620 may include a non-concentric portion 627 and a concentric portion 629. The non-concentric portion 627 may extend along at least a portion of a length of the sheath 620. In some examples, the non-concentric portion 627 may extend along the entire length of the sheath 620. The non-concentric portion 627 may have a thickness t1, and the concentric portion 629 may have a thickness t2. In some examples, the thickness t1 is greater than the thickness t2. The identification feature may be positioned within the non-concentric portion 627. In some examples, the identification feature may be one or more lumens 621 positioned within the non-concentric portion 627. While FIG. 7E shows three lumens 621 within the non-concentric portion 627, any number of lumens 621 may be included, such as one lumen, two lumens, four lumens, or any other number of lumens. In some examples, the lumens 621 may be filled with air or any other substance that may be visible in the image captured by the imaging probe 630.

Figure 7F:
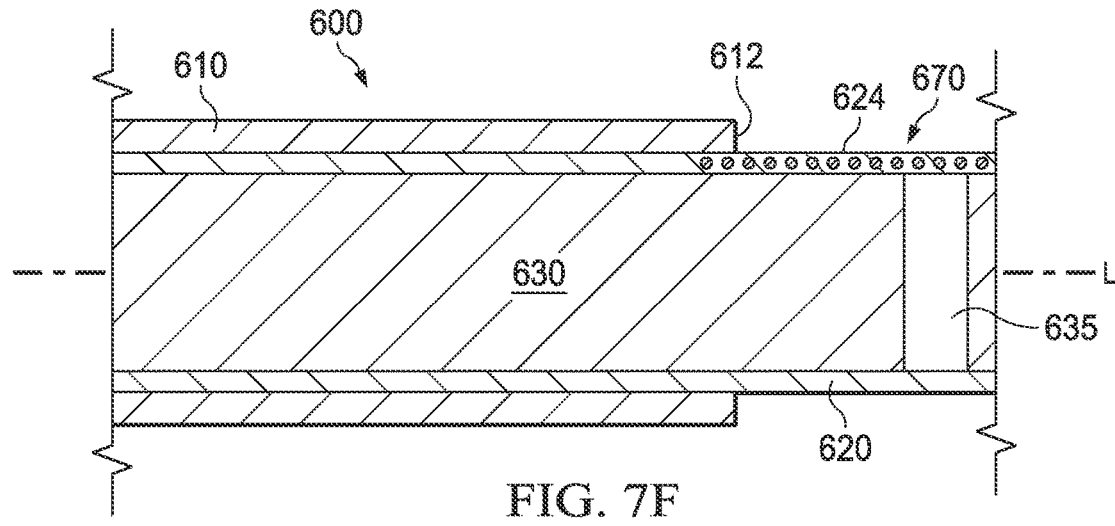

With reference now to FIG. 7F, the identification feature may be one or more markers 670. The markers 670 may be spherical, triangular, rectangular, star-shaped, and/or any other shape. In some examples, each of the markers 670 is the same shape (e.g., each marker is a sphere). Alternatively, one or more markers may be shaped differently than the other markers (e.g., some markers may be spheres, and some markers may be stars). The markers 670 may be aligned in a pattern that may be identified in the image captured by the imaging probe 630. In some examples, the markers 670 may be a first shape at a first insertion distance along the sheath 620 and may be a second shape at a second insertion distance along the sheath 620. For example, a portion of the markers 670 may be spheres, and a portion of the markers 670 may be stars. The spheres may be positioned distally of the stars in some examples. In other examples, the stars may be positioned distally of the spheres. As shown in FIG. 7F, the markers 670 may be positioned within the wall 622 of the sheath 620. Additionally or alternatively, the markers 670 may be positioned outside of the sheath 620, as discussed above with respect to FIG. 7B. The markers 670 may be aligned linearly or in any other manner, such as in a curve, in a circle, in one or more layers, and/or the like. In some examples, the markers 670 may be aligned parallel to a longitudinal axis of the sheath 620. In some alternative examples, the markers 670 may be aligned perpendicular to the longitudinal axis of the sheath 620.

In some examples, the markers 670 may be visible in an intraoperative external image (e.g., the intraoperative external image 830 in FIG. 10B) captured by an intraoperative external imaging device, such as a fluoroscopic imaging device, a CT imaging device, and/or the like. A processing system, such as an image processing system, may analyze the intraoperative external image to determine the insertion distance of the sheath 620 based on the markers 670. For example, the control system may determine how many markers 670 are extended beyond the distal end 612 of the catheter 610, which may indicate the insertion distance of the sheath 620. Additionally or alternatively, the markers 670 may be visible in the image captured by the imaging probe 630. A processing system, such as an image processing system, may analyze the captured image to determine the insertion distance of the sheath 620 based on the markers 670. For example, the control system may determine how many markers 670 are visible in the captured image, which may indicate the insertion distance of the sheath 620. In examples when the sheath 620 and the imaging probe 630 are axially constrained, the insertion distance of the sheath 620 may correspond to the insertion distance of the imaging probe 630.

In some examples, a proximal end of the imaging probe 630 may include one or more markers, which may be similar to the markers 670. As the imaging probe 630 is extended from the catheter 610 and/or from the sheath 620, the user and/or the control system may analyze the markers at the proximal end of the imaging probe 630 to determine the insertion distance of the imaging probe 630.

Figure 7G:
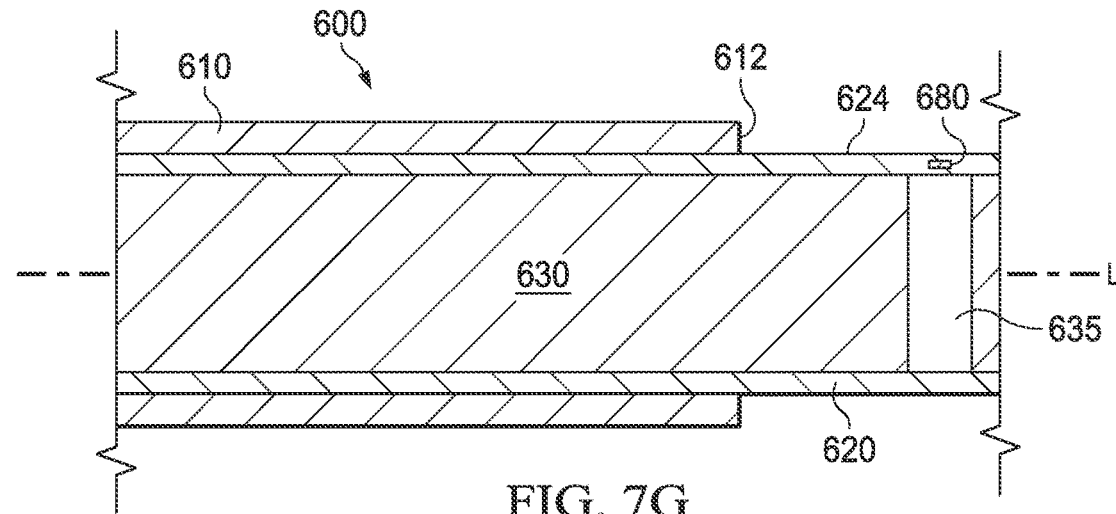

In some examples, as shown in FIG. 7G, the identification feature may be an active component 680, such as a transducer, an electromagnetic emitter, or any other active component. The active component 680 may emit a signal that is detectable by the control system. Based on the signal, the control system may determine the position and/or the rotational orientation of the sheath 620. In examples when the sheath 620 and the imaging probe 630 are rotationally constrained, the control system may determine the rotational orientation of the imaging probe 630 based on the signal received from the active component 680. In some examples, more than one active component 680 may be included at different axial positions along the length of the sheath 620 and/or at different radial positions around the circumference of the sheath 620. One or more of the active components may emit different signals, such as signals with different strengths and/or different frequencies. Based on the different signals received from the different active components 680, the control system may determine the rotational orientation and/or the insertion distance of the sheath 620. As discussed above, the active component(s) 680 may be positioned within the wall 622 of the sheath 620 or outside of the sheath 620.

Figure 7H:
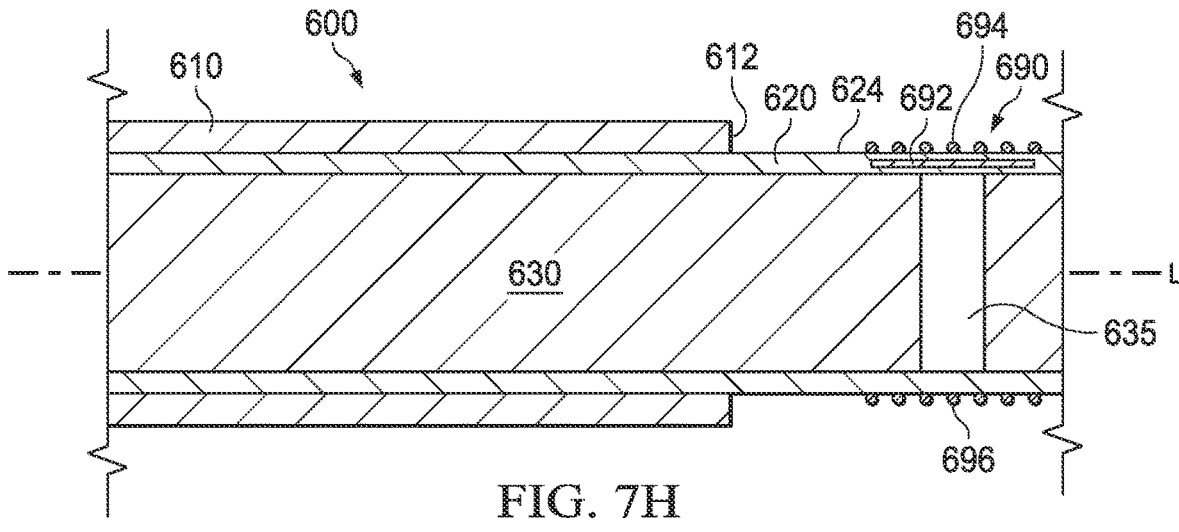

With reference to FIG. 7H, the identification feature may include a plurality of wires 690. The wires 690 may include one or more of an elongate wire 692, a helical wire 694, and/or a helical wire 696. The wires 690 may include any additional number of wires. In some examples, the wires 690 may include the elongate wire 692 and only one of the helical wire 694 or the helical wire 696. In some examples, the elongate wire 692 may be straight such that it is parallel with a longitudinal axis L of the imaging probe 630. While FIG. 7H shows the wire 692 within the wall 622 of the sheath 620 and the wires 694, 696 outside of the sheath 620, one, some, or all of the wires 690 may be positioned within the wall 622, outside of the sheath 620, or in any combination, as discussed above. Each of the wires 690 may be similar to the elongate wire 650 discussed above with respect to FIGS. 7B and 7C. The helical wires 694 and 696 may be coiled around the sheath 620, such as around the outer surface of the sheath 620 or within the wall of the sheath 620.

In some examples, one, some, or all of the wires 692-696 may be identified (by the control system and/or by the user) in the image captured by the imaging probe 630. As discussed above with respect to the elongate wire 650, the control system may determine the insertion distance of the imaging probe 630 based on the captured image of the wire 692. Additionally or alternatively, the control system may determine the rotational orientation of the sheath 620 based on the captured images of the wires 694, 696. For example, as the sheath 620 is inserted through the catheter 610, the imaging probe 630 (e.g., via the imaging device 635) may capture images of one or more of the wires 694, 696 at different rotational orientations. The different rotational orientations may indicate the insertion distance of the sheath 620. Additionally or alternatively, the images of the wires 694, 696 may indicate the bending of the sheath 620. For example, when the sheath 620 is bent, one side of the sheath 620 is compressed and the opposing side of the sheath 620 is stretched. The wires 694, 696 will similarly be compressed on one side and stretched on an opposing side. The spacing between the wires 694, 696 is greater on the side of the wire 694, 696 that is stretched than on the side of the wire 694, 696 that is compressed. Based on the spacing of the wires 694, 696 shown in the images of the wires 694, 696, the bending of the wires 694, 696 may be identified. The bending of the wires 694, 696 corresponds to the bending of the sheath 620. Therefore, the bending of the sheath 620 may be determined based on the bending of the wires 694, 696. In examples when the sheath 620 and the imaging probe 630 are rotationally constrained, the rotational orientation of the imaging probe 630 corresponds to the rotational orientation of the sheath 620.

Figures 8A, 8B, 8C, 8D:
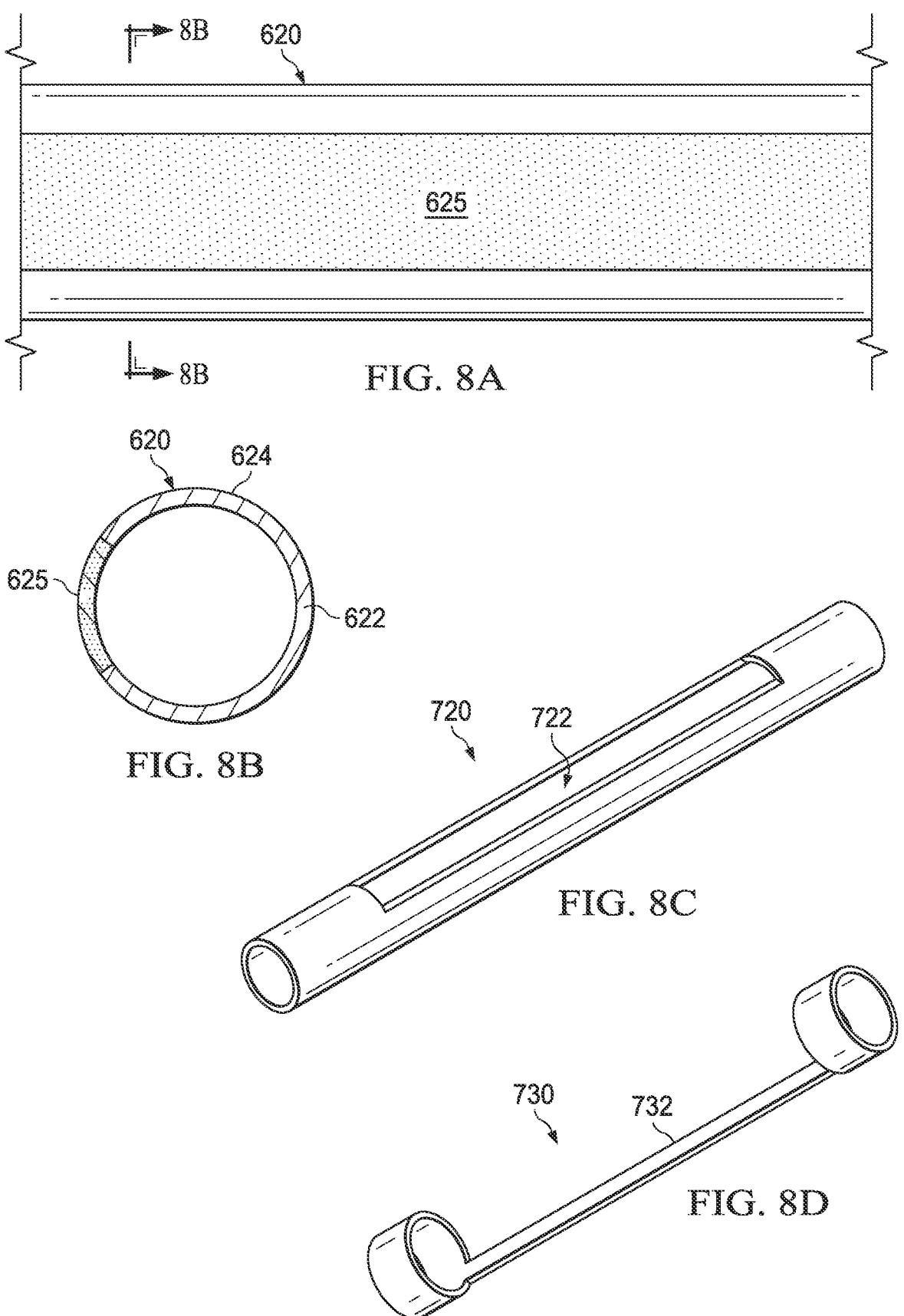
FIGS. 8A and 8B illustrate an imaging device with an imaging probe sheath with an identification feature according to some examples.
FIG. 8C illustrates an imaging device with an elongate slotted member positioned in an imaging probe sheath according to some examples.
FIG. 8D illustrates an imaging device with an elongate ribbon marker positioned in an imaging probe sheath according to some examples.

With reference now to FIGS. 8A and 8B, the identification feature may be a portion of the sheath 620 itself. For example, a portion 625 of the sheath 620 may be an identification feature and may be formed of a composite material. In some examples, the portion 625 may be formed as part of the wall 622 of the sheath 620. Alternatively, the portion 625 may be coupled to the outer surface 624 of the sheath 620. The composite material may be, for example, a combination of a non-attenuating polymer (e.g., one or more PEBA polymers or one or more polyurethane polymers, such as Tecoflex 80A) and an attenuating material (e.g., tungsten particles, gas bubbles, hollow glass microspheres, and/or the like). The portion 625 may extend along an entire length of the sheath 620, along separate portions of the length of the sheath 620, or along a portion of the sheath 620, such as the distal portion. The portion 625 may be visible in the image captured by the imaging probe 630. In some examples, the control system may identify the portion 625 in the image and determine a rotational orientation of the sheath 620 based on the identified portion 625.

In some examples, an elongate member, such as a hypo tube, may be positioned within or around the sheath 620. The hypo tube may act as the identification feature. Alternatively, the hypo tube may house the identification feature. In some examples, the hypo tube may act as one identification feature and may house one or more additional identification features. FIG. 8C illustrates an elongate member 720, which may be a hypo tube. The hypo tube 720 may be positioned within or around the sheath 620. When the imaging probe 630 is received by the sheath 620, the imaging probe 630 may be inserted through the hypo tube 720. The hypo tube 720 may include a slot 722, which may house any one or more of the identification features discussed above. The slot 722 may extend around any portion of the circumference of the hypo tube 720, such as one quarter of the circumference, one half of the circumference, three quarters of the circumference, or any other amount. In some examples, the hypo tube 720 may include slits in the wall of the hypo tube 720 to help increase the flexibility of the hypo tube 720 as the hypo tube 720 bends with the sheath 620. In some examples, the hypo tube 720 may be positioned at a distal portion of the sheath 620. The hypo tube 720 may be positioned such that the identification feature in the slot 722 is visible in the image captured by the imaging probe 630. In some examples, the hypo tube 720 itself may be the identification feature and may be visible in the image captured by the imaging probe 630.

FIG. 8D illustrates an elongate member 730, which may be a hypo tube. In some examples, the hypo tube 730 may be positioned within or around the sheath 620 and may replace the hypo tube 720. In some alternative examples, both hypo tubes 720, 730 may be positioned within or around the sheath 620. As discussed above with respect to the hypo tube 720, when the imaging probe 630 is received by the sheath 620, the imaging probe 630 may be inserted through the hypo tube 730. The hypo tube 730 may include a ribbon marker 732, which may be the identification feature. The ribbon marker 732 may extend around any portion of the circumference of the hypo tube 730, such as one tenth of the circumference, one quarter of the circumference, or any other amount. In some examples, the ribbon marker 732 may include slits to help increase the flexibility of the ribbon marker 732 as the ribbon marker 732 bends with the sheath 620. In some examples, the hypo tube 730 may be positioned at a distal portion of the sheath 620. The hypo tube 730 may be positioned such that the ribbon marker 732 is visible in the image captured by the imaging probe 630.

Turning to FIGS. 9A-9F, in some examples, the identification feature may be an expandable member. For example, when the sheath 620 is extended beyond the distal end 612 of the catheter 610, an identification feature 700 may radially expand from a collapsed position to an expanded position. The identification feature 700 may be in the collapsed position when the sheath is within the catheter 610. In some examples, the identification feature 700 is a balloon but may also be scaffolding, a spring-loaded feature, or any other expandable member. The balloon 700 itself may be detectable in the image captured by the imaging probe 630. Additionally or alternatively, a marker 710 may be coupled to the balloon 700. The marker 710 may be detectable in the image captured by the imaging probe 630. In some examples, the marker 710 may be a wire (similar to the elongate wire 650 discussed above with respect to FIGS. 7A and 7B) or may be any of the other identification features discussed above. In some examples, the marker 710 may be the identification feature.

Figure 9A:
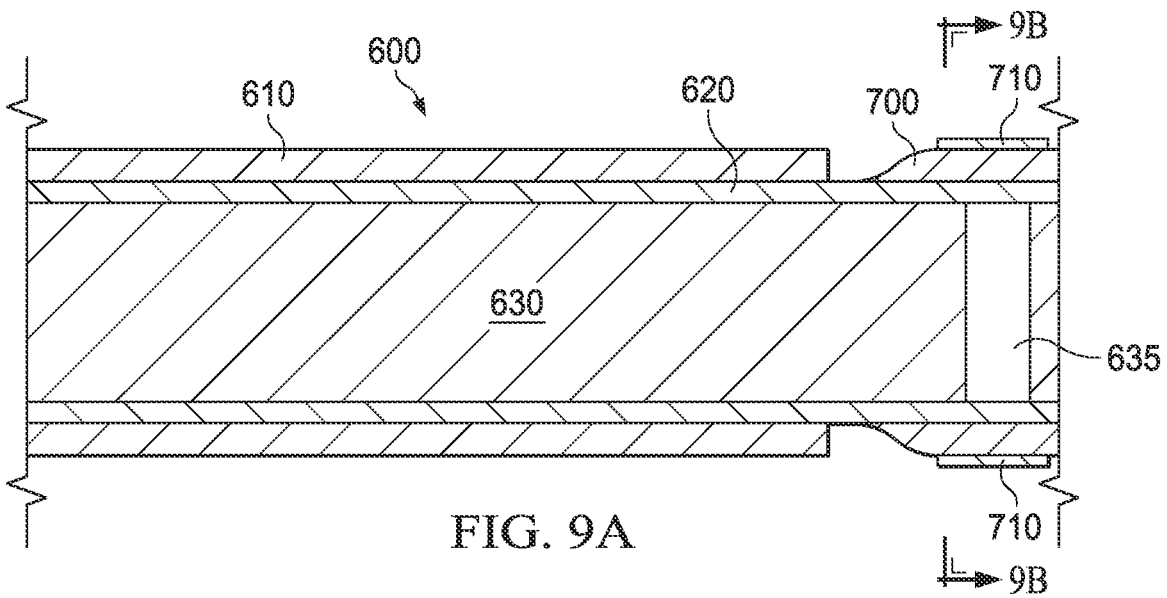
FIGS. 9A-9F illustrate an imaging device with an expandable feature coupled to an imaging probe sheath according to some examples.
Figure 9B:
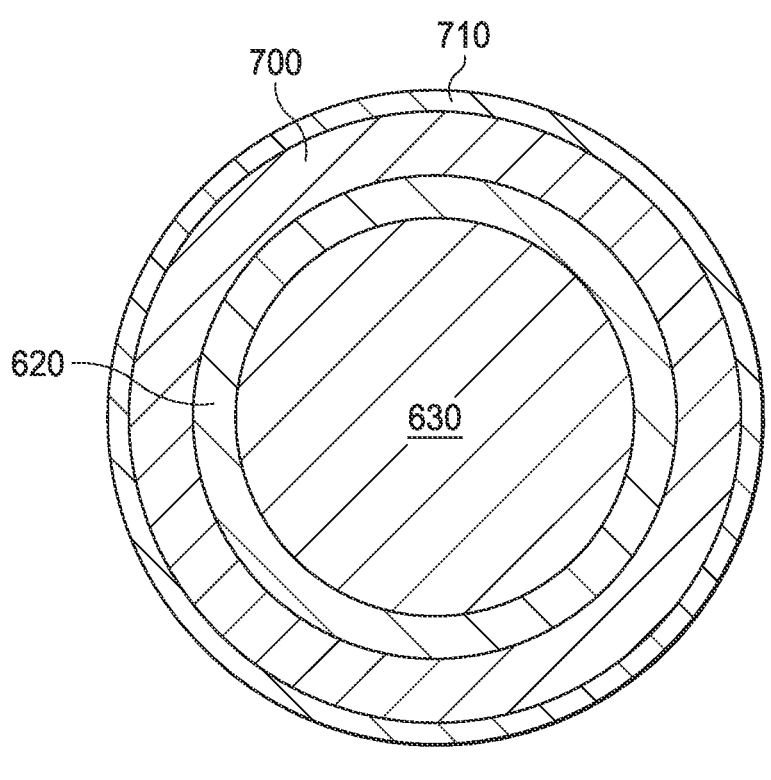
Figure 9C:
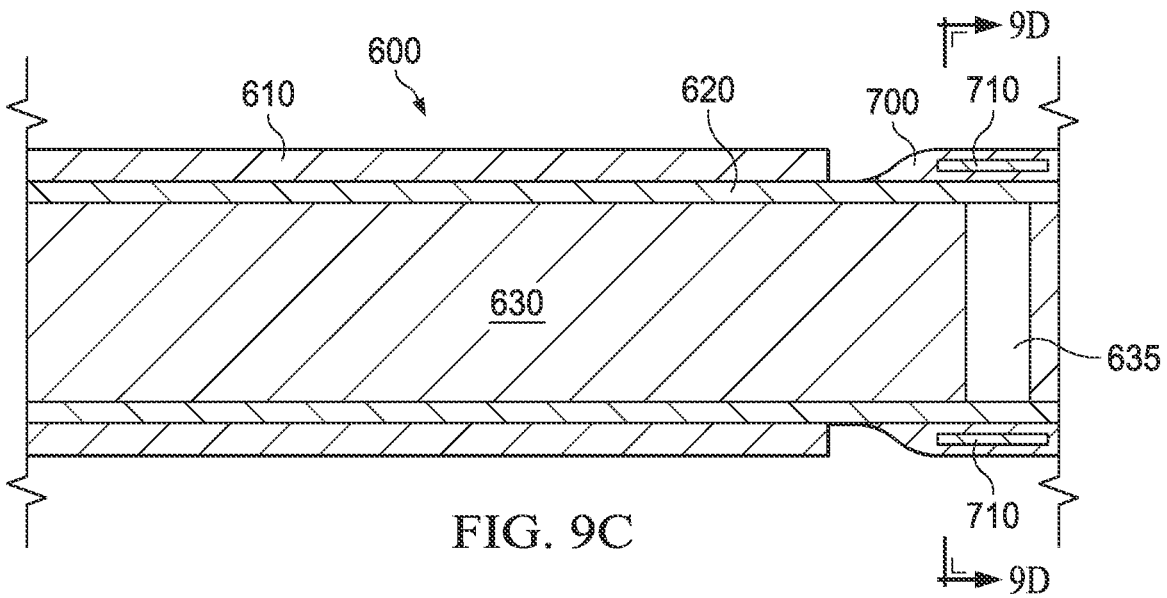
Figure 9D:
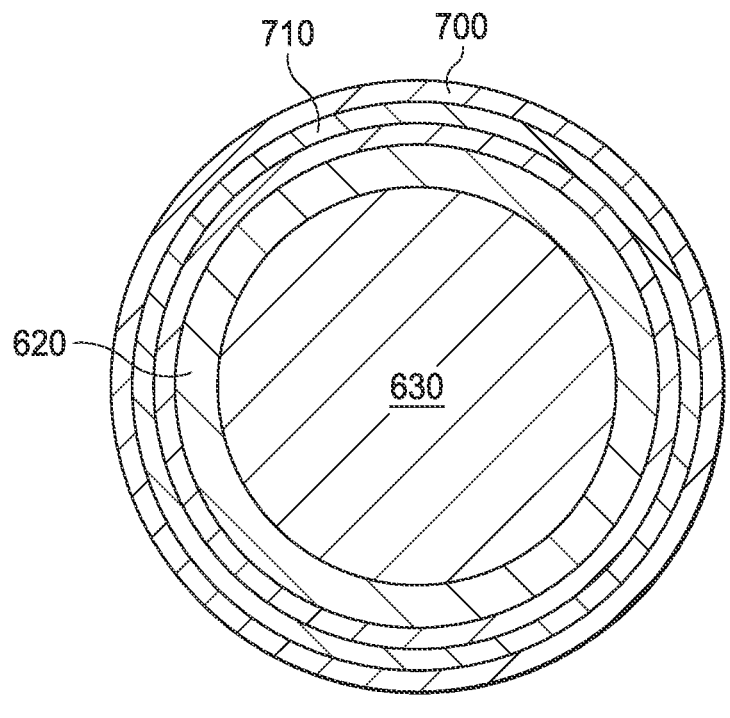

As shown in FIGS. 9A and 9B, the marker 710 may be coupled to an outside surface of the balloon 700. Additionally or alternatively, the marker 710 may be positioned within the balloon 700 (e.g., embedded within the balloon 700) as shown in FIGS. 7C and 7D. In some examples, the marker 710 may surround the balloon 700 such that the marker 710 is concentric with the balloon 700. Alternatively, the marker 710 may surround a portion of the balloon 700 (e.g., a portion of the circumference of the balloon).

Figure 9E:
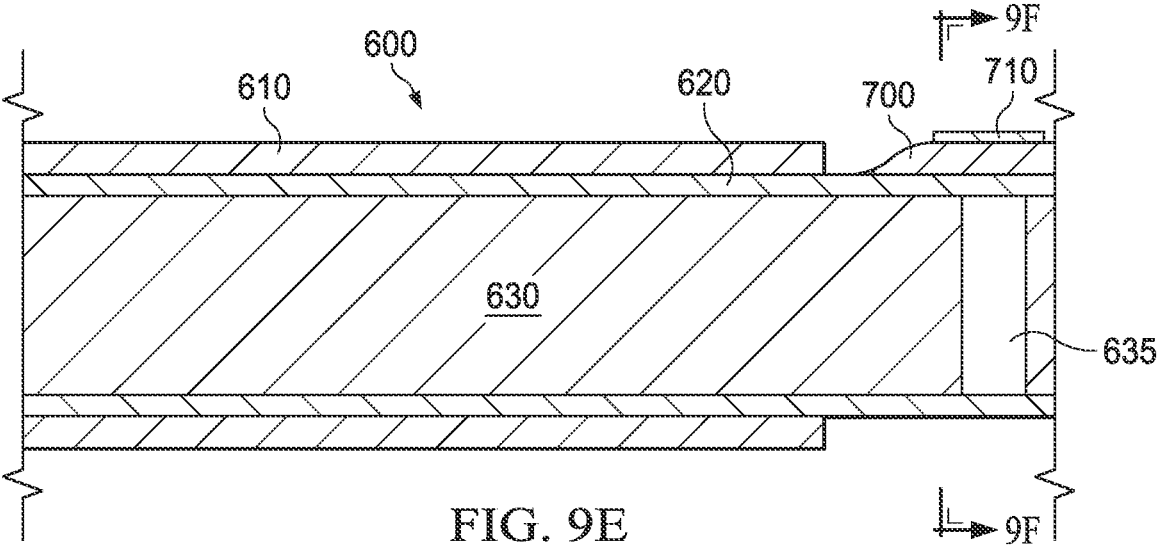
Figure 9F:
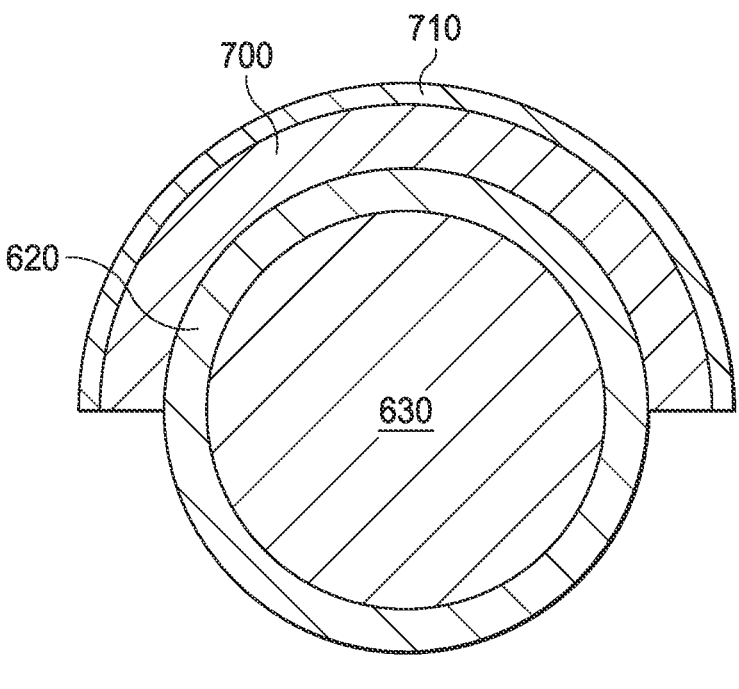

In some examples, the balloon 700 may surround a portion of the sheath 620 (e.g., a portion of a circumference of the sheath 620), as shown in FIGS. 9E and 9F. For example, the balloon 700 may surround half of the sheath 620, three-quarters of the sheath 620, one-quarter of the sheath 620, or any other amount of the sheath 620. In such examples, when the sheath 620 is extended out of the catheter 610 and the balloon 700 expands, the balloon 700 expands around the portion of the sheath 620 to which the balloon 700 is coupled. The expanded portion of the balloon 700 and/or the marker 710, which may be coupled to the balloon 700 as discussed above, may be identifiable in the image captured by the imaging probe 630.

In some examples, the balloon 700 may be pressurized based on the bending of the sheath 620. For example, one or more sensors, such as pressure sensors, shape sensors, or any other suitable sensor, may be positioned along the length of the sheath 620. When the sheath 620 bends, the control system may receive a signal from one or more of the sensors indicating which portion of the sheath 620 is bent. Based on this received sensor data, the control system may determine how the sheath 620 (and the imaging probe 630) is bent.

While the above discussion is made with respect to one balloon 700, multiple balloons (or other expandable features) may be coupled to the sheath 620 in some examples. In such examples, the balloons may be aligned parallel with a longitudinal axis of the sheath 620. In other examples, the balloons may form a spiral or other curved pattern around the sheath 620. As the sheath 620 is extended from the catheter 610, each balloon may expand as each balloon is extended beyond the distal end 612 of the catheter 610. The balloons may be identifiable in intraoperative external image data, such as fluoroscopic image data, that may be captured as the sheath 620 is extended from the catheter 610. In some examples, the control system and/or a user may analyze the intraoperative external image data to determine how many balloons have expanded. Based on the number of expanded balloons (and any partially expanded balloons), the control system and/or the user may determine the insertion distance of the sheath 620. In examples when the sheath 620 and the imaging probe 630 are axially constrained, the insertion distance of the sheath 620 may also correspond to the insertion distance of the imaging probe 630. In examples when the balloons form a spiral or other curved pattern around the sheath 620, the balloons may be identifiable in the intraoperative external image data at different angles around the circumference of the sheath 620.

Additionally or alternatively, the balloons may be identifiable in the intraoperative image captured by the imaging probe 630. For example, as the sheath 620 is extended from the catheter 610 and each balloon expands as it is extended beyond the distal end 612 of the catheter 610, each expanded balloon may be visible in the image captured by the imaging probe 630. In some examples, the control system and/or a user may analyze the intraoperative image to determine how many balloons have expanded. Based on the number of expanded balloons (and any partially expanded balloons), the control system and/or the user may determine how far the sheath 620 is extended from the catheter 610. In examples when the sheath 620 and the imaging probe 630 are axially constrained, the extension distance of the sheath 620 from the catheter 610 may also correspond to the extension distance of the imaging probe 630 from the catheter 610. In examples when the balloons form a spiral or other curved pattern around the sheath 620, the balloons may be identifiable in the intraoperative image at different angles around the circumference of the sheath 620.

As discussed above, the bending (e.g., pitch and/or yaw) of the imaging probe 630 relative to the longitudinal axis of the catheter 610 may be identified. In some examples, the balloons may be identifiable in the image captured by the imaging probe 630. In some examples, the control system and/or a user may analyze this image to determine how many balloons have expanded as the sheath 620 is extended from the catheter 610. Based on the number of expanded balloons (and any partially expanded balloons), the control system and/or the user may determine the bend angle (e.g., pitch and/or yaw) of the sheath 620. In some examples, the balloons may be actively controllable. For example, the control system may send signals to one or more of the balloons to control which balloons are expanded and/or the amount of expansion, such as any partial expansion, of the balloons. In some examples, the control system may control the expansion of one or more balloons over time such that the balloons are open and closed in a temporal pattern. For example, a distalmost balloon may be expanded and when it reaches full expansion, the adjacent balloon may be expanded. In some examples, when the adjacent balloon reaches full expansion, the distalmost balloon may be deflated. The control system may control the expansion of the balloons according to any other temporal pattern.

In some examples, as the sheath 620 bends, the amount of expansion of one or more of the balloons may change. The control system may detect these changes in expansion and may determine the bent orientation of the sheath 620 based on the received signals indicating the changes in expansion of the balloons. For example, the control system may receive one or more signals indicating that one or more balloons on one side of the sheath 620 are partially deflated and/or fully deflated. Based on these signals, the control system may determine that the side of the sheath 620 with the deflated balloons is bent. The control system may also determine the amount of bending based on the received signals.

While several examples of identification features are discussed above, any one or more similar identification features may be included in the imaging device 600. Additionally, any one or more of the identification features discussed above may be included, in any combination, in the imaging device 600. For example, the imaging device 600 may include an elongate wire (e.g., the elongate wire 650) and an expandable feature (e.g., the balloon 700).

In some examples, the identification feature may be visible in the raw imaging data (e.g., ultrasound data) received from the imaging probe 630, which may be an ultrasound imaging probe. A processing system, such as an image processor, and/or the control system may detect the identification feature in the raw imaging data to determine the rotational orientation of the image captured by the imaging probe 630 relative to the catheter 610, for example, using any one or more of the methods discussed above. The processing system may optionally "remove" the identification feature from the image that is displayed to the user such that the identification feature is not present in the image displayed to the user. In such examples, the processing system may detect the rotational orientation of the captured image, but the image displayed to the user is kept "clean." This may help declutter the displayed image and may allow the user to perform the medical procedure (or other procedure) more efficiently.

In some examples, the user may test the articulation of the catheter 610 and may observe how the image captured by the imaging probe 630 changes during the articulation. Based on the observed changes in the captured image, the user may determine the registration between the captured image and the catheter 610. For example, if the user articulates the catheter 610 to a "3:00" (i.e., 3 o'clock) orientation and the captured image indicates that the catheter 610 is oriented in a "9:00" orientation, then the user may determine that the articulation of the catheter 610 and the captured image are inversely related. In some examples, the control system may provide instructions to the user to perform this articulation after the control system and/or the user has identified the anatomical target (e.g., the target 314) in the image captured by the imaging probe 630. Additionally or alternatively, the control system may articulate the catheter 610 to determine the registration between the catheter 610 and the captured image. Additionally or alternatively, the control system may analyze the image captured by the imaging probe 630 to determine how the image captured by the imaging probe 630 changes during articulation of the catheter 610.

In some examples, a graphical user interface (GUI) may be used to assist with one or more aspects of the medical procedure. For example, an image of a medical instrument may be displayed on the GUI, and the position of the image of the medical instrument may be updated as the medical instrument is navigated through the patient anatomy. Additionally or alternatively, one or more images of an imaging device may be displayed on the GUI.

Figure 10A:
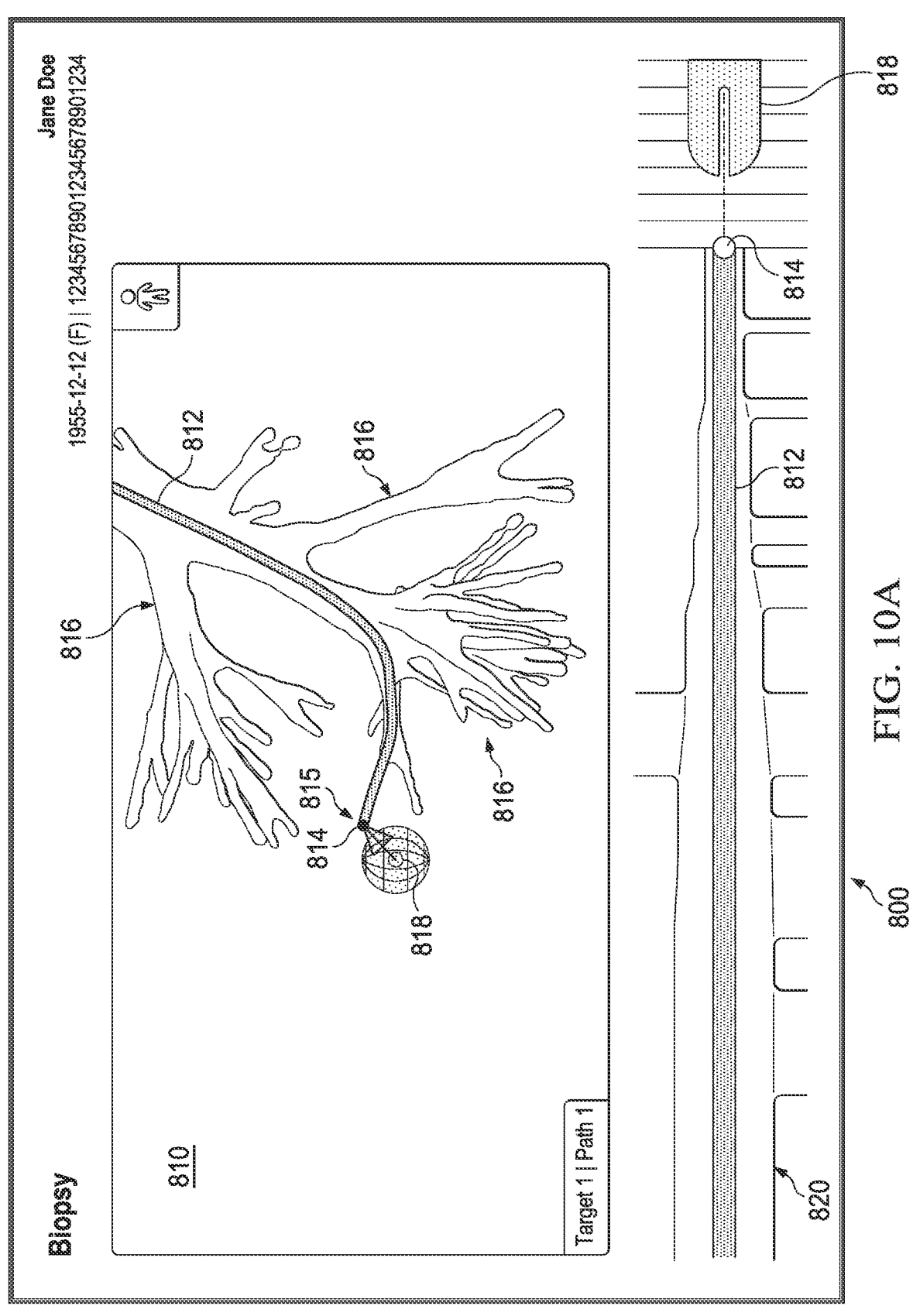
FIGS. 10A-10C illustrate a graphical user interface displaying a virtual navigation view according to some examples.
Figure 10B:
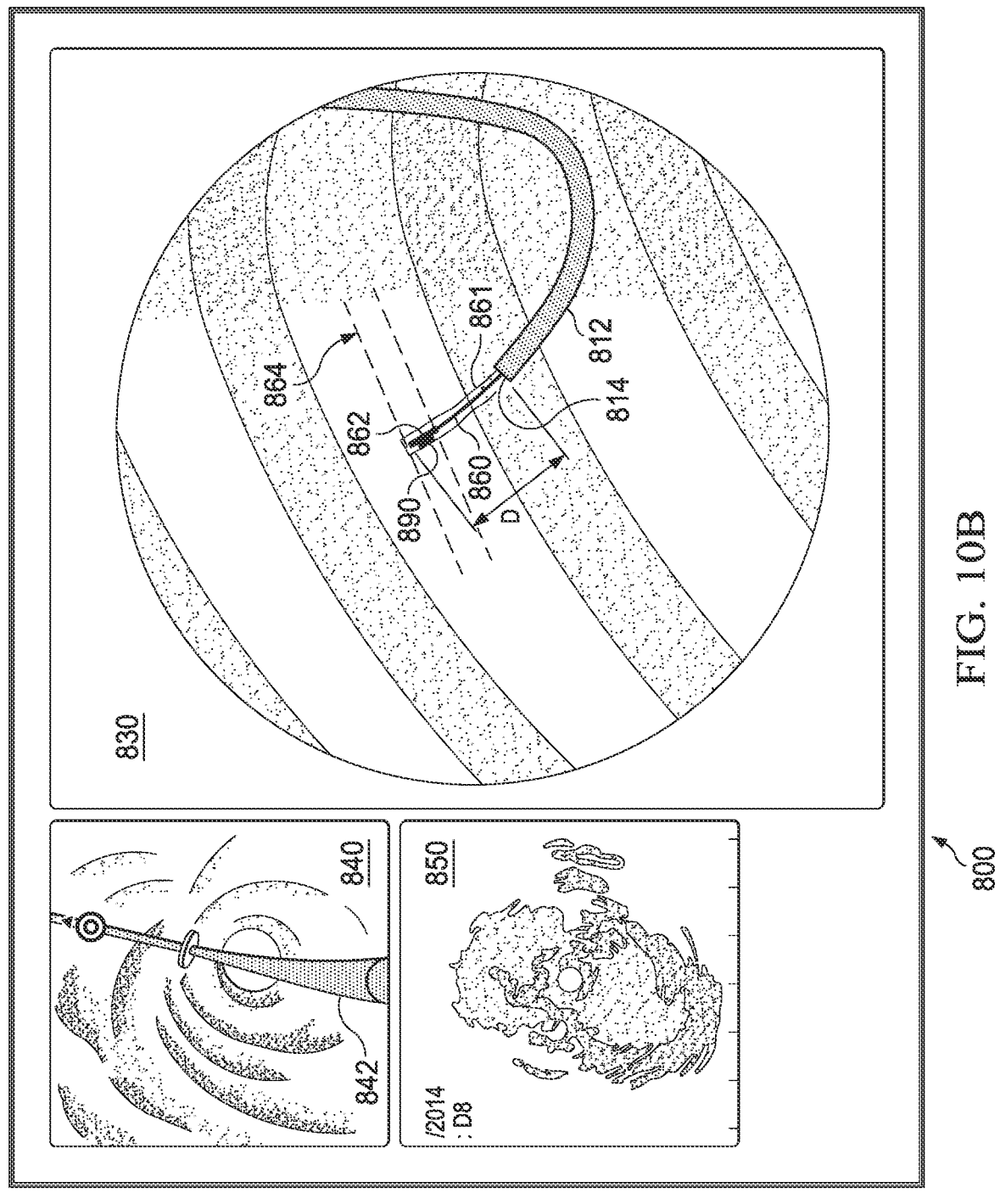
Figure 10C:
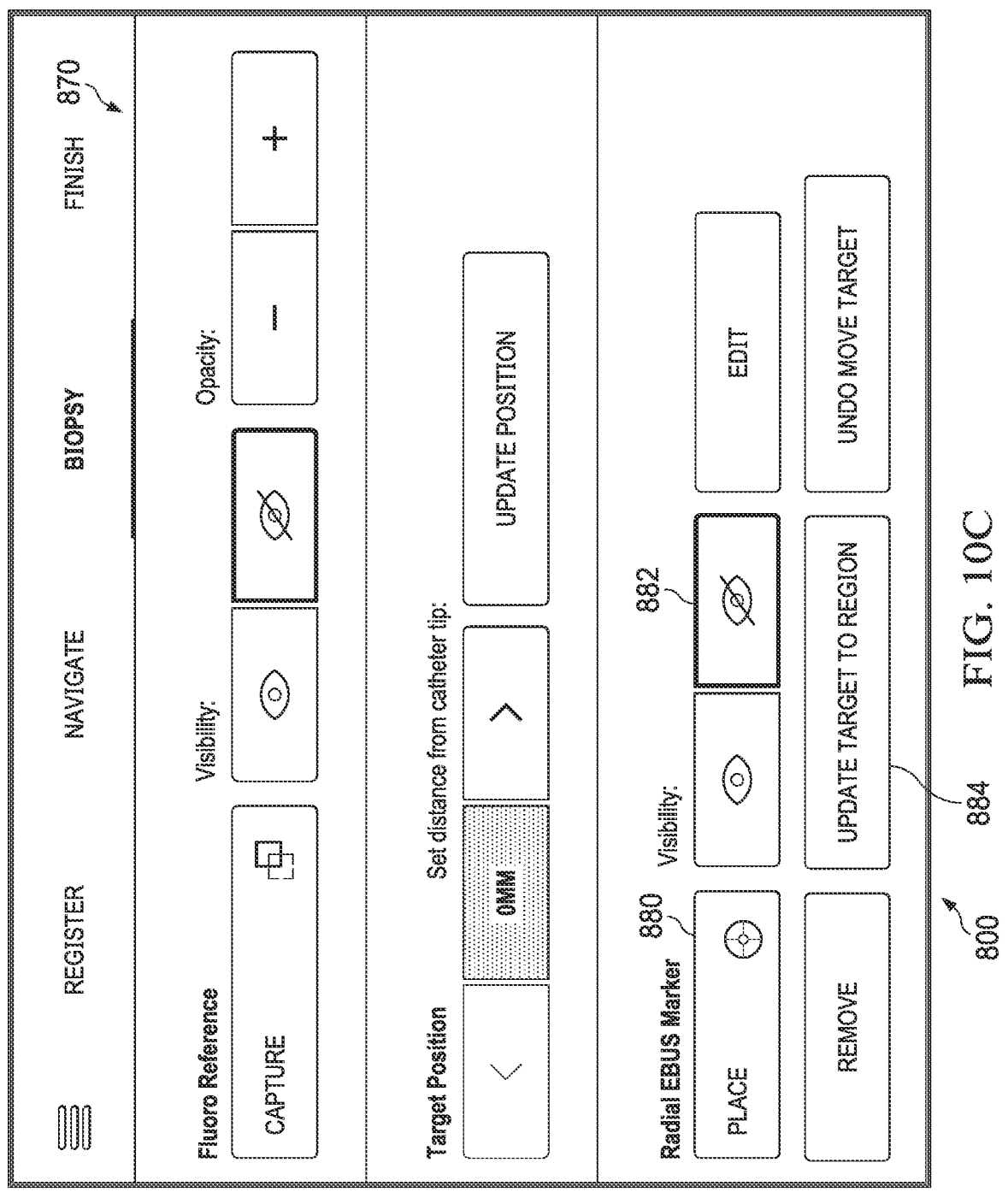

As shown in FIGS. 10A-10C, a graphical user interface (GUI) 800 includes a virtual navigation view 810. The virtual navigation view 810 may illustrate a medical instrument 812 (e.g., the medical instrument 104 of FIG. 1), one or more anatomical passageways 816, and an anatomical target 818 (e.g., the target 108 of FIG. 1). The virtual navigation view 810 may be generated by registering pre-operative image data (and a subsequently constructed 3D model) to a current location of the medical instrument 812. The GUI 800 may also include a reduced anatomical model 820, an intraoperative external image 830 (e.g., a fluoro-scopic image), a virtual path view 840, an intraoperative image 850, and an icon menu 870. The path view 840 may illustrate the view along a preoperatively planned traversal path 842 for the medical instrument 812 to follow through the anatomic passageways 816 identified in an anatomic model generated from preoperative image data (e.g., CT image data). The path view 840 may provide an interior view (e.g., a pseudo-endoscopic view) of one or more of the anatomic passageways 816 as the medical instrument 812 navigates the anatomic passageways 816 and may also selectively depict structures outside of the passageway walls, such as the target location, vasculature, pleura, or other anatomical structures. Further details of the GUI 800 may be found in the U.S. Provisional pat. app. No. 63/133, 091, filed on Dec. 31, 2020, entitled "Systems and Methods for Updating a Target Location Using Intraoperative Image Data," which is incorporated by reference herein in its entirety.

As shown in FIG. 10A, a distal end 814 of the medical instrument 812 may be navigated to an initial deployment location 815 near the anatomical target 818. The current shape of the medical instrument 812 and the location of the distal end 814 may be displayed in the virtual navigation view 810. Although illustrative arrangements of views are depicted in FIGS. 10A-10C, it is to be understood that the GUI 800 may display any number of views, in any arrangement, and/or on any number of screens. In some examples, the number of concurrently displayed views may be varied by opening and closing views, minimizing and maximizing views, moving views between a foreground and a background of the GUI 800, switching between screens, and/or otherwise fully or partially obscuring views. Similarly, the arrangement of the views—including their size, shape, orientation, ordering (in a case of overlapping views), and/or the like—may vary and/or may be user-configurable.

With reference to FIG. 10B, an imaging probe 860 (e.g., the imaging probe 630) and a sheath 861 (e.g., the sheath 620) may be deployed through a lumen of the medical instrument 812. A field of view of the imaging probe 860, which may be a field of view of an imaging device 862 (e.g., the imaging device 865), is illustrated as an imaging plane 864. As shown in FIG. 10B, the imaging plane 864 may be located at or near the distal end of the imaging probe 860.

In some examples, an insertion distance D of the imaging probe 860 may be measured by the control system. For example, the control system and/or an image processing system may analyze the intraoperative external image 830 to measure the insertion distance D. In some examples, the appearance of the identification feature 890 in the intraoperative external image 830 is different for different insertion distances of the imaging probe 860 relative to the sheath 861. The control system may determine the insertion distance of the imaging probe 860 relative to the sheath 861 based on the appearance of the identification feature 890 in the intraoperative external image 830.

Additionally or alternatively, the insertion distance D may be measured by a user and then input into the control system (e.g., via the GUI 800). For example, a sensor at a proximal portion of the imaging probe 860 may measure how far the distal end of the imaging probe 860 is extended from the distal end 814 of the medical instrument 812. Additionally or alternatively, a sensor at a proximal portion of the sheath 861 may measure how far the distal end of the imaging probe 860 is extended from the distal end 814 of the medical instrument 812. Additionally or alternatively, a sensor at a proximal portion of the sheath 861 may measure how far the distal end of the sheath 861 is extended from the distal end 814 of the medical instrument 812. Then, the control system and/or an image processing system may analyze the intraoperative external image 830 to determine how far into the sheath the imaging probe 860 is inserted to determine how far the distal end of the imaging probe 860 is extended from the distal end 814 of the medical instrument 812. Additionally or alternatively, a sensor at a proximal portion of the medical instrument 812 may measure how far the distal end of the imaging probe 860 is extended from the distal end 814 of the medical instrument 812. Other measurement techniques may be used without departing from the examples discussed herein.

Additionally or alternatively, the control system and/or the image processing system may analyze the intraoperative external image 830 to determine the off-axis bending (e.g., the pitch and/or the yaw) of the imaging probe 860. In some examples, the control system and/or the image processing system may analyze the intraoperative external image 830 to determine the orientation of the imaging device 862 at the distal end of the imaging probe 860. As discussed above, the imaging device 862 may be a radial EBUS transducer that rotates to obtain one or more ultrasound images. In some examples, the orientation of the imaging device 862 may be seen in the intraoperative external image 830 when the imaging device 862 is not rotating. As further discussed above, the image captured by the imaging probe 860 may include an image of an identification feature, which may be present on an imaging probe sheath (e.g., the sheath 620 of FIGS. 7A-7H). In some examples, the identification feature, such as an identification feature 890, may be visible in the intraoperative external image 830 (e.g., when the identification feature is a radiopaque marker). The control system may analyze the intraoperative external image 830 to compare the orientation of the identification feature with the orientation of the imaging device 862. Based on this comparison, the control system may determine the orientation of the imaging probe 860 relative to the medical instrument 812. In some examples, the appearance of the identification feature 890 in the intraoperative external image 830 is different for different off-axis bending orientations of the sheath 861. The control system may determine the off-axis bending of the imaging probe 860 based on the appearance of the identification feature 890 in the intraoperative external image 830.

The imaging probe 860 may include a shape sensor, which may extend along a length of the imaging probe 860. In some additional examples, the medical instrument 812 may include a shape sensor. Based on shape data received from the shape sensor of the imaging probe 860, the control system may determine the shape of the imaging probe 860. Based on shape data received from the shape sensor of the medical instrument 812, the control system may determine the shape of the medical instrument 812. In some examples, the control system may compare the shape of the imaging probe 860 to the shape of the medical instrument 812 to determine the insertion distance of the imaging probe 860 relative to the medical instrument 812. For example, the control system may determine how far the imaging probe 860 is extended beyond the distal end 814 of the medical instrument 812. Additionally or alternatively, based on shape data received from the shape sensor of the imaging probe 860, the control system may determine the pitch and/or the yaw of the imaging probe 860.

In some examples, a proximal end of the imaging probe 860 may include a transmission mechanism that allows for finer adjustment of the insertion distance of the imaging probe 860. For example, the transmission mechanism may allow for larger insertion movements at the proximal end of the imaging probe 860 to translate to smaller insertion movements at the distal end of the imaging probe 860. For example, if the proximal end of the imaging probe 860 is inserted 2 cm, the distal end of the imaging probe 860 may be inserted 1 mm. Any other insertion distance ratio may be achieved by the transmission mechanism.

Additionally or alternatively, the user may insert the imaging probe 860 by a known insertion distance. The control system may receive an input from the user (e.g., via the GUI 800) inputting the insertion distance. Additionally or alternatively, the control system may provide instructions to the user to insert the imaging probe 860 by a specified distance, such as 5 mm, 10 mm, 15 mm, or any other distance. In such examples, the insertion distance may be known by the control system but may still be determined/confirmed by the control system using any one or more of the methods discussed above.

In examples when the control system provides instructions to the user to insert the imaging probe 860 by a small distance (e.g., 2 mm, 3 mm, 4 mm), the imaging probe 860 may not bend or may experience negligible bending when the imaging probe 860 is extended from the medical instrument 812. In such examples, the control system may determine that there is no bending in the imaging probe 860. For example, the control system may determine that a longitudinal axis of the imaging probe 860 is substantially parallel with a longitudinal axis of the medical instrument 812 when the imaging probe 860 is extended from the medical instrument 812. In some alternative examples when the imaging probe 860 may be bent a negligible amount, the control system may determine the amount of bending in the imaging probe 860 using any one or more of the methods discussed above.

As discussed above, the control system may determine the position of the medical instrument 812 within the anatomical passageways 816. Based on this position information, the control system may determine in which anatomical passageway 816 the medical instrument 812 is positioned. In some examples, the control system may determine the shape of a portion of the anatomical passageway 816 within which the medical instrument 812 is positioned that is more distal than the portion of the anatomical passageway 816 within which the medical instrument 812 is positioned. Additionally or alternatively, the control system may determine the shape of any one or more anatomical passageways extending distally of the anatomical passageway 816 within which the medical instrument 812 is positioned. For example, the control system may analyze the model of the patient anatomy that was generated based on preoperative imaging data, as discussed above. Based on the knowledge of the distally extending anatomical passageway(s), the control system may predict how the imaging probe 860 will bend when the imaging probe 860 is extended out from the medical instrument 812. In some examples, the control system may predict how the imaging probe 860 will bend to assist with identifying the orientation of the imaging plane (e.g., by identifying the orientation of the imaging probe 860).

When the imaging probe 860 is extended from the medical instrument 812, the imaging probe 860 may bend toward a path of least resistance, which may be a path that most closely follows a flow of fluid through the anatomical passageways. In some examples, the anatomical passageway 816 may include a branch point, such as a carina, at the distal end of the anatomical passageway 816. In some examples, the branch point may separate two anatomical passageways. If the medical instrument 812 is oriented toward one of the anatomical passageways, the control system may predict that the imaging probe 860 will bend toward that anatomical passageway when the imaging probe 860 is extended from the medical instrument 812. If the medical instrument 812 is oriented toward the other anatomical passageway, the control system may predict that the imaging probe 860 will bend toward that anatomical passageway when the imaging probe 860 is extended from the medical instrument 812.

With reference to FIG. 10C, a target adjustment procedure may be initiated when the control system receives a user input selecting a "Place" icon 880 in the icon menu 870 of the GUI 800. The target adjustment procedure may use the intraoperative imaging data received from the imaging probe

860 to adjust the position of the target 818 in the virtual navigation view 810, as discussed above with respect to process 422 of FIG. 4.

In some examples, the components discussed above may be part of a robotic-assisted system as described in further detail below. The robotic-assisted system may be suitable for use in, for example, surgical, robotic-assisted surgical, diagnostic, therapeutic, or biopsy procedures. While some examples are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic, general robotic-assisted, or robotic medical systems.

Figure 11:
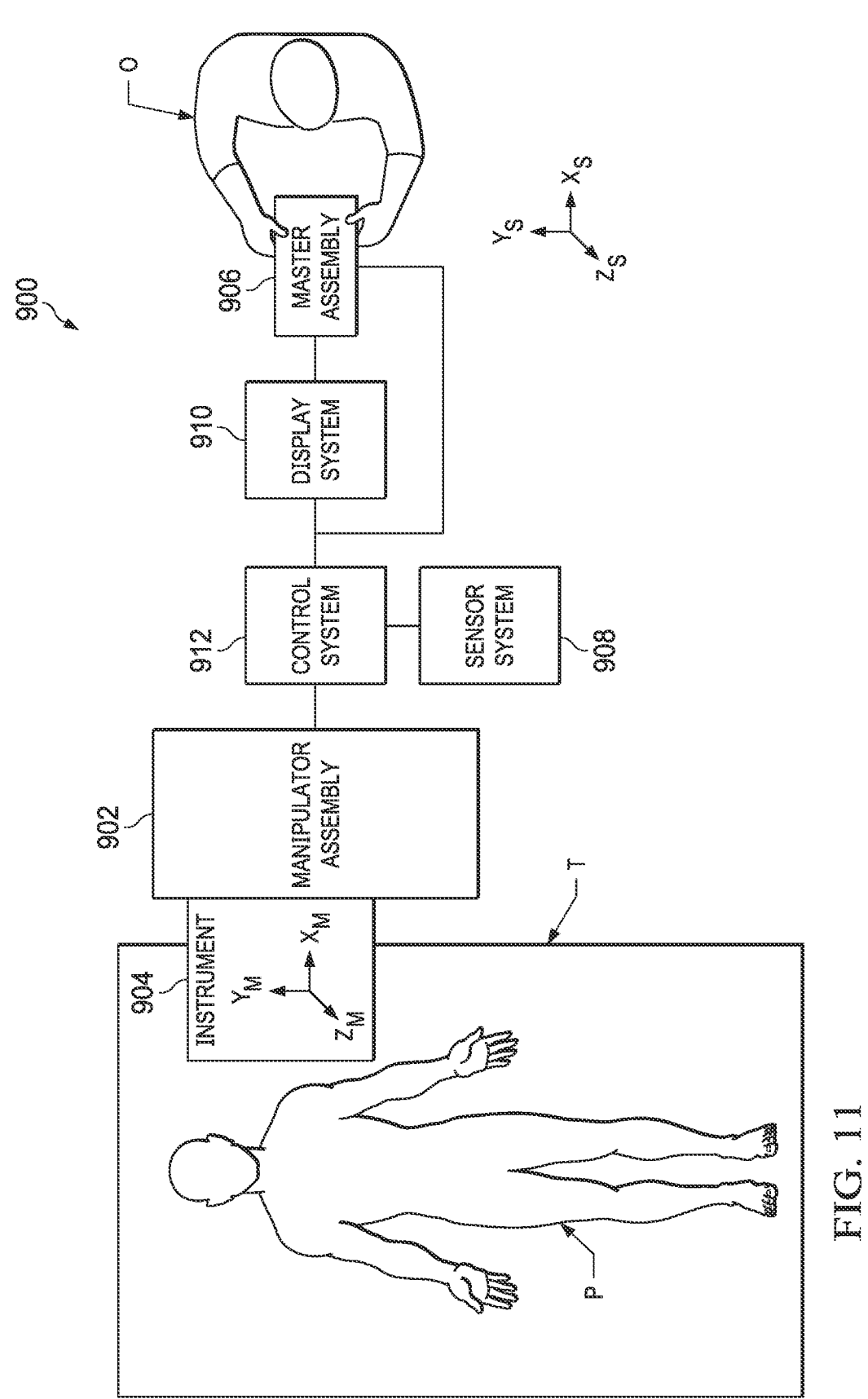
FIG. 11 is a simplified diagram of a robotic-assisted medical system according to some examples.

As shown in FIG. 11, a medical system 900 generally includes a manipulator assembly 902 for operating a medical instrument 904 (e.g., the medical instrument 104) in performing various procedures on a patient P positioned on a table T. The manipulator assembly 902 may be robotic-assisted, non-robotic-assisted, or a hybrid robotic-assisted and non-robotic-assisted assembly with select degrees of freedom of motion that may be motorized and/or robotic-assisted and select degrees of freedom of motion that may be non-motorized and/or non-robotic-assisted. The medical system 900 may further include a master assembly 906, which generally includes one or more control devices for controlling manipulator assembly 902. Manipulator assembly 902 supports medical instrument 904 and may optionally include a plurality of actuators or motors that drive inputs on medical instrument 904 in response to commands from a control system 912. The actuators may optionally include drive systems that when coupled to medical instrument 904 may advance medical instrument 904 into a naturally or surgically created anatomic orifice.

Medical system 900 also includes a display system 910 for displaying an image or representation of the surgical site and medical instrument 904 generated by sub-systems of sensor system 908. Display system 910 and master assembly 906 may be oriented so operator O can control medical instrument 904 and master assembly 906 with the perception of telepresence. Additional information regarding the medical system 900 and the medical instrument 904 may be found in International Application Publication No. WO 2018/195216, filed on Apr. 18, 2018, entitled "Graphical User Interface for Monitoring an Image-Guided Procedure," which is incorporated by reference herein in its entirety.

In some examples, medical instrument 904 may include components of an imaging system (discussed in more detail below), which may include an imaging scope assembly or imaging instrument that records a concurrent or real-time image of a surgical site and provides the image to the operator or operator O through one or more displays of medical system 900, such as one or more displays of display system 910. The concurrent image may be, for example, a two or three-dimensional image captured by an imaging instrument positioned within the surgical site. In some examples, the imaging system includes endoscopic imaging instrument components that may be integrally or removably coupled to medical instrument 904. However, in some examples, a separate endoscope, attached to a separate manipulator assembly may be used with medical instrument 904 to image the surgical site. In some examples, as described in detail below, the imaging instrument alone or in combination with other components of the medical instrument 904 may include one or more mechanisms for cleaning one or more lenses of the imaging instrument when the one or more lenses become partially and/or fully obscured by fluids and/or other materials encountered by the distal end of the imaging instrument. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in International Application Publication No. WO/2016/025465, filed on Aug. 11, 2016, entitled "Systems and Methods for Cleaning an Endoscopic Instrument"; U.S. patent application Ser. No. 15/508,923, filed on Mar. 5, 2017, entitled "Devices, Systems, and Methods Using Mating Catheter Tips and Tools"; and U.S. patent application Ser. No. 15/503,589, filed Feb. 13, 2017, entitled "Systems and Methods for Cleaning an Endoscopic Instrument," each of which is incorporated by reference herein in its entirety. The imaging system may be implemented as hardware, firmware, software or a combination thereof which interact with or are otherwise executed by one or more computer processors, which may include the processors of the control system 912.

Control system 912 includes at least one memory and at least one computer processor (not shown) for effecting control between medical instrument 904, master assembly 906, sensor system 908, and display system 910. Control system 912 also includes programmed instructions (e.g., a non-transitory machine-readable medium storing the instructions) to implement some or all of the methods described in accordance with aspects disclosed herein, including instructions for providing information to display system 910.

Figure 12:
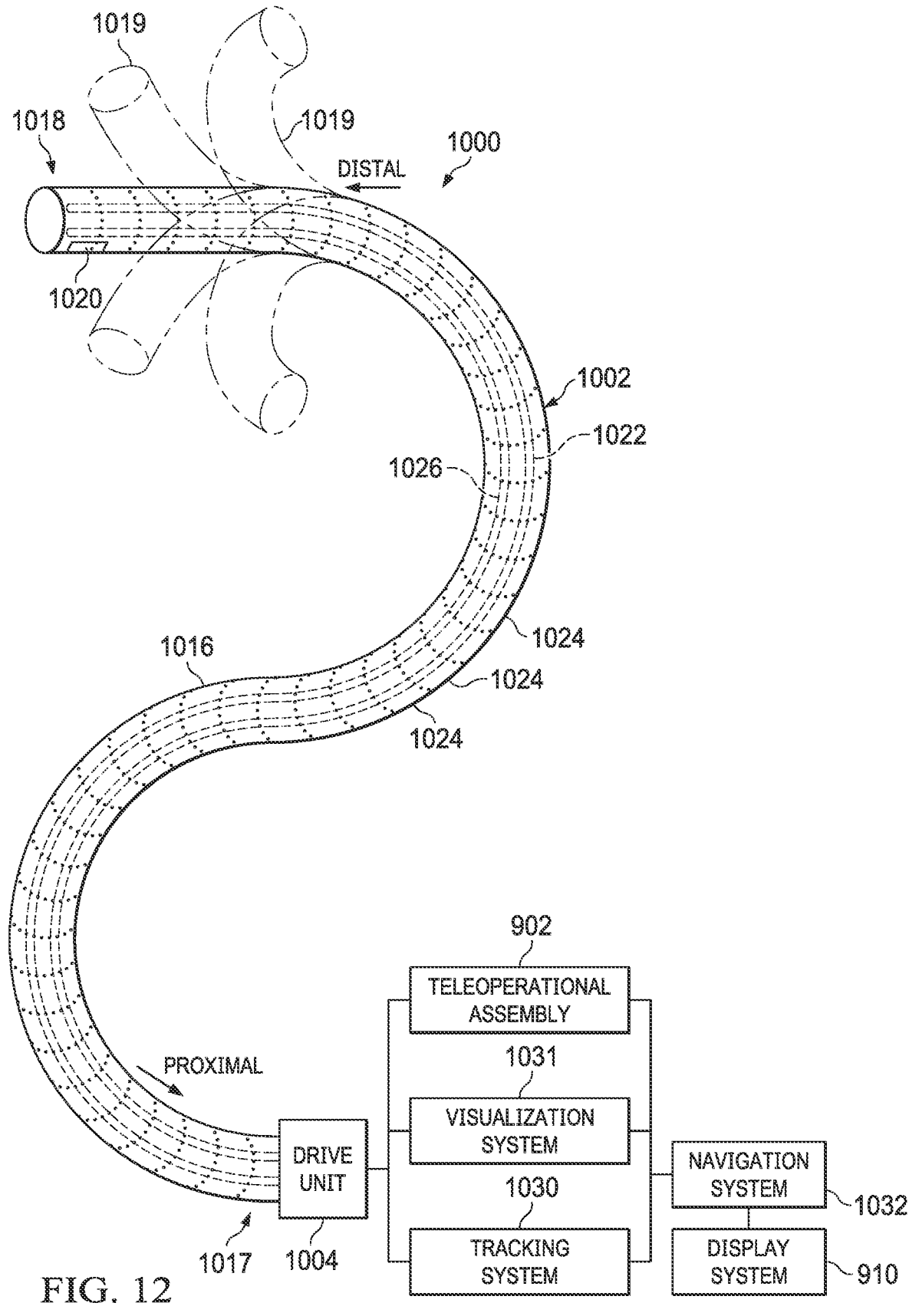
FIG. 12 is a simplified diagram of a medical instrument system according to some examples.

FIG. 12 is a simplified diagram of a medical instrument system 1000 according to some examples. Medical instrument system 1000 includes elongate device 1002, such as a flexible catheter (e.g., the outer catheter 320), coupled to a drive unit 1004. Elongate device 1002 includes a flexible body 1016 having proximal end 1017 and distal end or tip portion 1018. Medical instrument system 1000 further includes a tracking system 1030 for determining the position, orientation, speed, velocity, pose, and/or shape of distal end 1018 and/or of one or more segments 1024 along flexible body 1016 using one or more sensors and/or imaging devices as described in further detail below.

Tracking system 1030 may optionally track distal end 1018 and/or one or more of the segments 1024 using a shape sensor 1022. Shape sensor 1022 may optionally include an optical fiber aligned with flexible body 1016 (e.g., provided within an interior channel (not shown) or mounted externally). The optical fiber of shape sensor 1022 forms a fiber optic bend sensor for determining the shape of flexible body 1016. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed on Jul. 13, 2005, entitled "Fiber Optic Position and Shape Sensing Device and Method Relating Thereto"; U.S. patent application Ser. No. 12/047,056, filed on Jul. 16, 2004, entitled "Fiber-Optic Shape and Relative Position Sensing"; and U.S. Pat. No. 6,389,187, filed on Jun. 17, 1998, entitled "Optical Fibre Bend Sensor", each of which is incorporated by reference herein in its entirety. Sensors in some examples may employ other suitable strain sensing techniques, such as Rayleigh scattering, Raman scattering, Brillouin scattering, and Fluorescence scattering. In some examples, the shape of the elongate device may be determined using other techniques. For example, a history of the distal end pose of flexible body 1016 can be used to reconstruct the shape of flexible body 1016 over the interval of time. In some examples, tracking system 1030 may optionally and/or additionally track distal end 1018 using a position sensor system 1020. Position sensor system 1020 may be a component of an EM sensor system with position sensor system 1020 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some examples, position sensor system 1020 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732, filed on Aug. 11, 1999, entitled "Six-Degree of Freedom Tracking System Having a Passive Transponder on the Object Being Tracked", which is incorporated by reference herein in its entirety.

Flexible body 1016 includes a channel 1021 sized and shaped to receive a medical instrument 1026. Further description of a medical instrument received by a flexible body is provided in U.S. Provisional Patent Application No. 63/077,059, filed on Sep. 11, 2020, entitled "Systems for Coupling and Storing an Imaging Instrument", which is incorporated by reference herein in its entirety.

Flexible body 1016 may also house cables, linkages, or other steering controls (not shown) that extend between drive unit 1004 and distal end 1018 to controllably bend distal end 1018 as shown, for example, by broken dashed line depictions 1019 of distal end 1018. In some examples, at least four cables are used to provide independent "up-down" steering to control a pitch of distal end 1018 and "left-right" steering to control a yaw of distal end 1018. Steerable elongate devices are described in detail in U.S. patent application Ser. No. 13/274,208, filed on Oct. 14, 2011, entitled "Catheter with Removable Vision Probe", which is incorporated by reference herein in its entirety.

The information from tracking system 1030 may be sent to a navigation system 1032 where it is combined with information from image processing system 1031 and/or the preoperatively obtained models to provide the operator with real-time position information. In some examples, the real-time position information may be displayed on display system 910 of FIG. 11 for use in the control of medical instrument system 1000. In some examples, control system 912 of FIG. 11 may utilize the position information as feedback for positioning medical instrument system 1000. Various systems for using fiber optic sensors to register and display a surgical instrument with surgical images are provided in U.S. patent application Ser. No. 13/107,562, filed on May 13, 2011, entitled "Medical System Providing Dynamic Registration of a Model of an Anatomic Structure for Image-Guided Surgery," which is incorporated by reference herein in its entirety.

In some examples, medical instrument system 1000 may be robotic-assisted within medical system 900 of FIG. 11. In some examples, manipulator assembly 902 of FIG. 11 may be replaced by direct operator control. In some examples, the direct operator control may include various handles and operator interfaces for hand-held operation of the instrument.

The singular forms "a", "an", and "the" are intended to include the plural forms as well, unless the context indicates otherwise. And the terms "comprises," "comprising," "includes," "has," and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. The auxiliary verb "may" likewise implies that a feature, step, operation, element, or component is optional.

In the description, specific details have been set forth describing some embodiments. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

Elements described in detail with reference to one example, implementation, or application optionally may be included, whenever practical, in other examples, implementations, or applications in which they are not specifically shown or described. For example, if an element is described in detail with reference to one example and is not described with reference to a second example, the element may nevertheless be claimed as included in the second example. Thus, to avoid unnecessary repetition in the following description, one or more elements shown and described in association with one example, implementation, or application may be incorporated into other examples, implementations, or aspects unless specifically described otherwise, unless the one or more elements would make an example or implementation non-functional, or unless two or more of the elements provide conflicting functions.

Any alterations and further modifications to the described devices, instruments, methods, and any further application of the principles of the present disclosure are fully contemplated as would normally occur to one skilled in the art to which the disclosure relates. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The systems and methods described herein may be suited for navigation and treatment of anatomic tissues, via natural or surgically created connected passageways, in any of a variety of anatomic systems, including the lung, colon, the intestines, the kidneys and kidney calices, the brain, the heart, the circulatory system including vasculature, and/or the like. Although some of the examples described herein refer to surgical procedures or instruments, or medical procedures and medical instruments, the techniques disclosed apply to non-medical procedures and non-medical instruments. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical medical treatment or diagnosis procedures.

Further, although some of the examples presented in this disclosure discuss robotic-assisted systems or remotely operable systems, the techniques disclosed are also applicable to computer-assisted systems that are directly and manually moved by operators, in part or in whole.

Additionally, one or more elements in examples of this disclosure may be implemented in software to execute on a processor of a computer system such as a control processing system. When implemented in software, the elements of the examples of the present disclosure are essentially the code segments to perform the necessary tasks. The program or code segments can be stored in a processor readable storage medium (e.g., a non-transitory storage medium) or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit, a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller" or "control system", are analogous.

Note that the processes and displays presented may not inherently be related to any particular computer or other apparatus, and various systems may be used with programs in accordance with the teachings herein. The required structure for a variety of the systems discussed above will appear as elements in the claims. In addition, the examples of the present disclosure are not described with reference to any particular programming language. It will be appreciated that a variety of programming languages may be used to implement the teachings of the present disclosure as described herein.

While certain example examples of the present disclosure have been described and shown in the accompanying drawings, it is to be understood that such examples are merely illustrative of and not restrictive to the broad disclosed concepts, and that the examples of the present disclosure not be limited to the specific constructions and arrangements shown and described, since various other modifications may occur to those ordinarily skilled in the art.

What is claimed is:

1. A medical system comprising:
an elongate device;
an elongate sheath configured to extend within the elongate device, the elongate sheath including an identification feature;
an imaging probe configured to extend within the elongate sheath; and
a control system configured to:
    receive imaging data from the imaging probe, the imaging data being captured by the imaging probe;
    analyze the imaging data to identify an appearance of the identification feature within the imaging data; and
    based on the appearance of the identification feature:
        register the imaging data to a reference frame of the elongate device; and
        determine (a) an off-axis bending of the imaging probe or (b) an insertion distance of the imaging probe relative to the elongate sheath as the imaging probe is extended within the sheath.

2. The medical system of claim 1, wherein:
the elongate sheath is slidably insertable relative to the elongate device;
the imaging probe is slidably insertable relative to the elongate sheath;
a distal end of the elongate sheath is configured to extend distally of a distal end of the elongate device; and
a distal end of the imaging probe is configured to extend distally of the distal end of the elongate sheath.

3. The medical system of claim 1, wherein the imaging probe comprises an ultrasound probe, and wherein the imaging data comprises an ultrasound image.

4. The medical system of claim 1, wherein the control system is configured to register the imaging data to the reference frame of the elongate device by identifying a rotational orientation of the imaging data relative to the elongate device.

5. The medical system of claim 4, wherein:
the elongate device includes a keyed feature and the elongate sheath includes a corresponding keyed feature that receives the keyed feature to fix a rotational orientation of the elongate sheath to a rotational orientation of the elongate device; and
identifying the rotational orientation of the imaging data relative to the elongate device comprises:
    determining a rotational orientation of the imaging data relative to the rotational orientation of the elongate sheath based on the appearance of the identification feature within the imaging data; and
    determining the rotational orientation of the imaging data relative to the rotational orientation of the elongate device based on the fixed rotational orientation of the elongate sheath to the rotational orientation of the elongate device.

6. The medical system of claim 1, wherein:
the appearance of the identification feature within the imaging data is different for different off-axis bending of the elongate sheath.

7. The medical system of claim 1, wherein:
the appearance of the identification feature within the imaging data is different for different insertion distances of the imaging probe relative to the elongate sheath.

8. The medical system of claim 1, wherein the control system is configured to register the imaging data to the reference frame of the elongate device by determining the insertion distance of the imaging probe relative to the elongate device based on the insertion distance of the imaging probe relative to the elongate sheath and an insertion distance of the elongate sheath relative to the elongate device.

9. The medical system of claim 1, wherein the appearance of the identification feature within the imaging data comprises at least one of:
a shape of the identification feature within the imaging data; or
a location of the identification feature within the imaging data.

10. The medical system of claim 1, wherein the control system is further configured to register one or more objects captured in the imaging data to the reference frame of the elongate device based on the appearance of the identification feature.

11. The medical system of claim 1, wherein the control system is further configured to register, based on the registration of the imaging data to the reference frame of the elongate device, at least one of:
a position of the imaging probe to the reference frame of the elongate device; or
a position of the elongate sheath to the reference frame of the elongate device.

12. The medical system of claim 1, wherein the identification feature comprises an elongate wire.

13. The medical system of claim 1, wherein the identification feature is positioned within a wall of the elongate sheath.

14. The medical system of claim 13, wherein:
a non-concentric portion of the wall of the elongate sheath extends radially outward from a longitudinal axis of the elongate sheath;
a first portion of the identification feature is positioned within a concentric portion of the wall;
a second portion of the identification feature is positioned within the non-concentric portion of the wall;
the first portion of the identification feature is a first thickness; and
the second portion of the identification feature is a second thickness different from the first thickness.

15. The medical system of claim 1, wherein the identification feature is coupled to an outer surface of the elongate sheath.

16. The medical system of claim 1, wherein the identification feature is configured to emit a signal, and wherein the control system is configured to analyze the signal to determine a rotational orientation of the imaging data relative to the elongate device.

17. The medical system of claim 1, wherein the identification feature includes a pattern of markers.

18. The medical system of claim 1, wherein the identification feature comprises an expandable member configured to radially expand when the elongate sheath is extended distally from a distal end of the elongate device.

19. The medical system of claim 1, wherein:

the imaging probe includes a shape sensor; and the control system is configured to determine a shape of the imaging probe based on shape data captured by the shape sensor.

20. The medical system of claim 19, wherein the control system is further configured to determine, based on the shape data, at least one of:

a rotational orientation of the imaging data relative to the elongate device; or an insertion distance of a distal end of the imaging probe relative to a distal end of the elongate device.

21. A method comprising:

receiving imaging data from an imaging probe, the imaging data being captured by the imaging probe, wherein the imaging probe is configured to extend within an elongate sheath, the elongate sheath configured to extend within an elongate device, the elongate sheath including an identification feature;

analyzing the imaging data to identify an appearance of the identification feature within the imaging data; and based on the appearance of the identification feature:

registering the imaging data to a reference frame of the elongate device; and determining (a) an off-axis bending of the imaging probe or (b) an insertion distance of the imaging probe relative to the elongate sheath as the imaging probe is extended within the sheath.

22. The method of claim 21, further comprising registering the imaging data to the reference frame of the elongate device by identifying a rotational orientation of the imaging data relative to the elongate device.

23. The method of claim 21, wherein the appearance of the identification feature within the imaging data is different for different off-axis bending of the elongate sheath.

24. The method of claim 21, wherein the appearance of the identification feature within the imaging data is different for different insertion distances of the imaging probe relative to the elongate sheath.

* * * * *